United States Patent
Bermond et al.

(10) Patent No.: US 11,730,752 B2
(45) Date of Patent: Aug. 22, 2023

(54) USE OF NMN FOR THE PREVENTION AND/OR TREATMENT OF JOINT PAIN INDUCED BY PHYSICAL ACTIVITY, AND CORRESPONDING COMPOSITIONS

(71) Applicant: NUVAMID SA, Nyon (CH)

(72) Inventors: Guillaume Bermond, Marseilles (FR); Laurent Garcon, Sausset les Pins (FR)

(73) Assignee: NUVAMID SA, Nyon (CH)

( * ) Notice: Subject to any disclaimer, the term of this patent is extended or adjusted under 35 U.S.C. 154(b) by 0 days.

(21) Appl. No.: 17/791,092

(22) PCT Filed: Jan. 12, 2021

(86) PCT No.: PCT/EP2021/050499
§ 371 (c)(1),
(2) Date: Jul. 6, 2022

(87) PCT Pub. No.: WO2021/144274
PCT Pub. Date: Jul. 22, 2021

(65) Prior Publication Data
US 2023/0060438 A1 Mar. 2, 2023

(30) Foreign Application Priority Data
Jan. 13, 2020 (FR) .................................. FR2000270

(51) Int. Cl.
| | | |
|---|---|---|
| A01N 43/04 | (2006.01) | |
| A61K 31/70 | (2006.01) | |
| A61K 31/706 | (2006.01) | |
| A61P 19/02 | (2006.01) | |
| A61P 29/00 | (2006.01) | |
| A61K 45/06 | (2006.01) | |

(52) U.S. Cl.
CPC ............ *A61K 31/706* (2013.01); *A61K 45/06* (2013.01); *A61P 19/02* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 10,618,927 B1 * | 4/2020 | Szczepankiewicz | .. A61K 45/06 |
| 2017/0080011 A1 | 3/2017 | Fu et al. | |
| 2017/0189434 A1 | 7/2017 | Normington et al. | |
| 2017/0266213 A1 | 9/2017 | Fu et al. | |
| 2021/0230208 A1 | 7/2021 | Marcuccio et al. | |
| 2021/0309685 A1 | 10/2021 | Marcuccio et al. | |

FOREIGN PATENT DOCUMENTS

| | | | | |
|---|---|---|---|---|
| WO | WO-2006001982 A2 * | 1/2006 | ........... | A61K 31/405 |
| WO | 2019/222360 | 11/2019 | | |
| WO | 2019/222368 | 11/2019 | | |

OTHER PUBLICATIONS

Di Stefano, M., et al. "A rise in NAD precursor nicotinamide mononucleotide (NMN) after injury promotes axon degeneration." Cell Death & Differentiation 22.5 (2015): 731-742.*
Yoshino et al. Cell Metabolism (2011), vol. 14, pp. 528-536.*
Chen, Weiqian, Caihong Yi, and Lin Jin. "The role of nicotinamide adenine dinucleotide in the pathogenesis of rheumatoid arthritis: potential implications for treatment." EMJ 3.3 (2018): 90-97.*
Shinde, Chetan G., et al. "Methotrexate: a gold standard for treatment of rheumatoid arthritis." Journal of pain & palliative care pharmacotherapy 28.4 (2014): 351-358.*
Criswell, Lindsey, et al. "Moderate-term, low-dose corticosteroids for rheumatoid arthritis." Cochrane Database of Systematic Reviews 3 (1998).*
β-Nicotinamide Mononucleotide (β-NMN, Cas No. 1094-61-7) Cayman Chemical.
Migaud, M.E., et al., "Probing Aplysia californica Adenosine 5¢-Diphosphate Ribosyl Cyclase for Substrate Binding Requirements: Design of Potent Inhibitors," Biochemistry, 1999, vol. 38, pp. 9105-9114.

* cited by examiner

*Primary Examiner* — Patrick T Lewis
(74) *Attorney, Agent, or Firm* — Duane Morris LLP; Gregory M. Lefkowitz; Brandon A. Chan

(57) ABSTRACT

The invention relates to nicotinamide mononucleotide, a pharmaceutically acceptable derivative thereof, or a pharmaceutically acceptable salt thereof, for use in preventing and/or treating joint pain induced by physical activity, and compositions comprising same.

15 Claims, 1 Drawing Sheet

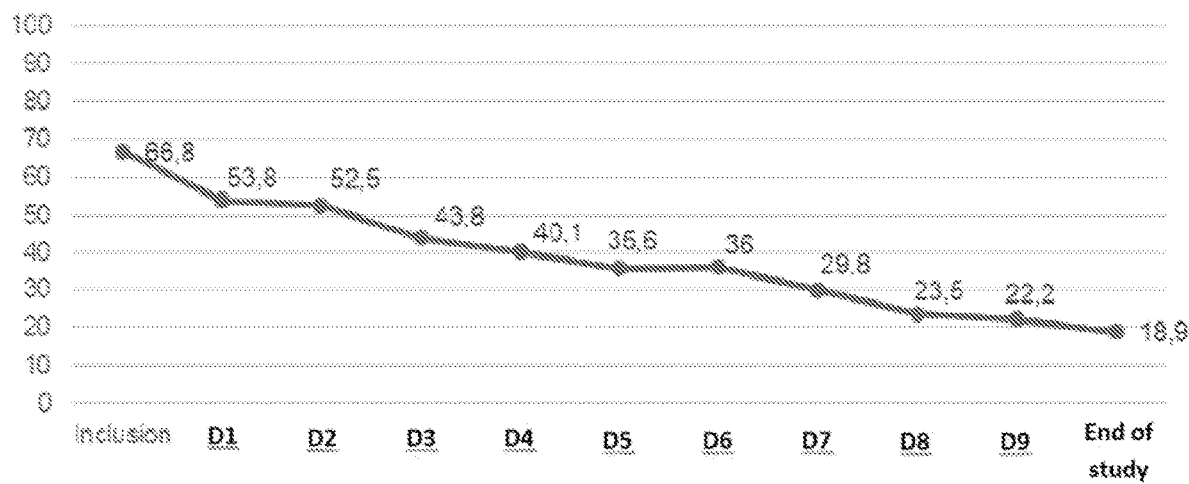

USE OF NMN FOR THE PREVENTION AND/OR TREATMENT OF JOINT PAIN INDUCED BY PHYSICAL ACTIVITY, AND CORRESPONDING COMPOSITIONS

CROSS-REFERENCE TO RELATED APPLICATIONS

This application is a § 371 national stage entry of International Application No. PCT/EP2021/050499, filed Jan. 12, 2021, which claims priority to French Patent Application No. FR2000270, filed Jan. 13, 2020, the entire contents of which are incorporated herein by reference.

FIELD OF THE INVENTION

The present invention relates to the use of nicotinamide mononucleotide (NMN), a pharmaceutically acceptable derivative thereof, or a pharmaceutically acceptable salt thereof, and compositions comprising same, for the prevention and/or treatment of joint pain, preferably gonalgia, induced by physical activity, in particular sporting activities.

TECHNICAL BACKGROUND

Physical activity, and in particular playing sports, helps to maintain a good physical condition and to improve health. The WHO provides global recommendations relating to physical activity for health, varying in duration and intensity according to the age of the subject (available under the ISBN number: 9789241599979).

However, exercising excessively, with poor execution, or with improper equipment can lead to joint pain. For example joint pain in the elbow, shoulder, and knee are common in tennis. Joint pain in the knees is also common for runners, especially when running in the city on terrain that is particularly hard on the joints or when their shoes are not suitable. Golfers may also experience shoulder, back, or knee pain.

Joint pain can also occur when maintaining bad posture for too long, for example when crouching for a long time while gardening or doing DIY. In the same way, repetitive movements while working can cause joint pain. For example, climbing up and down a stepladder to put away products in a storeroom can cause knee or shoulder pain.

Such pain is not caused by an underlying pathological condition such as osteoarthritis, an inflammatory pathology such as arthritis or cartilage inflammation, a tumor, an autoimmune disease, osteopathy, chondropathy, etc. They are also not caused by a traumatic condition such as a fracture, sprain, dislocation, or contusion, unless induced by playing sports.

Such pain is usually transient, localized, and not very intense. Treatment of such pain is often self-medicating and usually involves administering analgesics, non-steroidal anti-inflammatory drugs (NSAIDs), or cortisone derivatives, either topically or orally.

However, administering these drugs harms, inter alia, the stomach, the liver, and the kidneys. In addition, their effectiveness decreases over time, requiring an increase in dosage. In addition, chronic use of cortisone derivatives induces in particular bone fragility, neuropsychiatric effects, muscle loss, and reduced immunity, leaving the patient vulnerable to infections.

Thus, there is a need to develop new compositions for treating and/or preventing joint pain induced by physical activity, particularly sports, that reduce the drawbacks of the prior art.

SUMMARY OF THE INVENTION

These objectives are achieved by the invention as described below.

The present invention relates to nicotinamide mononucleotide (NMN), a pharmaceutically acceptable derivative thereof, or a pharmaceutically acceptable salt thereof, for topical use in preventing and/or treating joint pain induced by physical activity.

Advantageously, the pharmaceutically acceptable NMN derivative may be selected from a compound of formula (I):

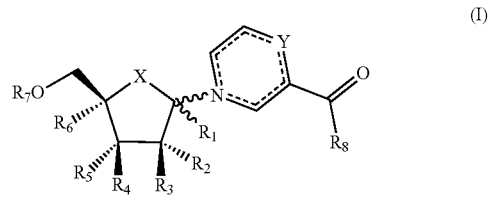

or a stereoisomer, salt, hydrate, solvate, or pharmaceutically acceptable crystal thereof, wherein:

X is selected from O, $CH_2$, S, Se, CHF, $CF_2$ and $C=CH_2$;

$R_1$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$ alkyl;

$R_2$, $R_3$, $R_4$, and $R_5$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR; wherein R is selected from H, $C_1$-$C_{12}$ alkyl, $C(O)(C_1$-$C_{12})$alkyl, $C(O)NH(C_1$-$C_{12})$alkyl, $C(O)O(C_1$-$C_{12})$alkyl, C(O)aryl, $C(O)(C_1$-$C_{12})$aryl alkyl, $C(O)NH(C_1$-$C_{12})$aryl alkyl, $C(O)O(C_1$-$C_{12})$aryl alkyl, and $C(O)CHR_{AA}NH_2$; wherein $R_{AA}$ is a side chain selected from a proteinogenic amino acid;

$R_6$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$alkyl;

$R_7$ is selected from H, $P(O)R_9R_{10}$, $P(S)R_9R_{10}$, and

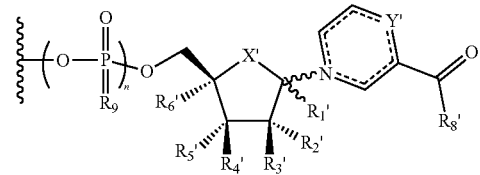

where n is an integer selected from 1, 2, or 3; wherein
  $R_9$ and $R_{10}$ are independently selected from OH, $OR_{11}$, $NHR_{13}$, $NR_{13}R_{14}$, $C_1$-$C_8$ alkyl, $C_2$-$C_8$ alkenyl, $C_2$-$C_8$ alkynyl, $C_3$-$C_{10}$ cycloalkyl, $C_5$-$C_{12}$, aryl $(C_1$-$C_8)$aryl alkyl, $(C_1$-$C_8)$aryl alkyl, $(C_1$-$C_8)$ heteroalkyl, $(C_1$-$C_8)$ heterocycloalkyl, heteroaryl, and $NHCHR_AR_AC(O)R_{12}$; wherein:
  $R_{11}$ is selected from $C_1$-$C_{10}$ alkyl, $C_3$-$C_{10}$ cycloalkyl, $C_5$-$C_{18}$ aryl, $C_1$-$C_{10}$ alkyl aryl, $C_5$-$C_{12}$ substituted aryl, $C_1$-$C_{10}$ heteroalkyl, $C_3$-$C_{10}$ heterocycloalkyl, $C_1$-$C_{10}$ haloalkyl, heteroaryl, $—(CH_2)_n$ $C(O)(C_1$-

$C_{15}$)alkyl, —(CH$_2$)$_n$ OC(O)(C$_1$-C$_{15}$)alkyl, —(CH$_2$)$_n$ OC(O)O(C$_1$-C$_{15}$)alkyl, —(CH$_2$)$_n$ SC(O)(C$_1$-C$_{15}$)alkyl, —(CH$_2$)$_n$ C(O)O(C$_1$-C$_{15}$)alkyl and —(CH$_2$)$_n$ C(O)O(C$_1$-C$_{15}$)alkyl aryl; $_{16\ 16\ 2}$ wherein n is an integer selected from 1 to 8; P(O)(OH)OP(O)(OH)$_2$; halogen, nitro, cyano, C$_1$-C$_6$ alkoxy, C$_1$-C$_6$ haloalkoxy, —N(R$_{11a}$)$_2$, C$_1$-C$_6$ acylamino, —COR$_{11b}$, —OCOR$_{11b}$; NHSO$_2$ (C$_1$-C$_6$ alkyl), —SO$_2$N(R$_{11a}$)$_2$SO$_2$ wherein each of R$_{11a}$ is independently selected from H and C$_1$-C$_6$ alkyl and R$_{11b}$ is independently selected from OH, C$_1$-C$_6$ alkoxy, NH$_2$, NH(C xml-ph-002

R$_{12}$ is selected from H, C$_1$-C$_{10}$ alkyl, C$_2$-C$_8$ alkenyl, C$_2$-C$_8$ alkynyl, C$_1$-C$_{10}$ haloalkyl, C$_3$-C$_{10}$ cycloalkyl, C$_3$-C$_{10}$ heterocycloalkyl, C$_5$-C$_{15}$ aryl, C$_1$-C$_4$ alkyl aryl and C$_5$-C$_{12}$ heteroaryl; wherein said aryl or heteroaryl groups are optionally substituted with one or two groups selected from halogen, trifluoromethyl, C$_1$-C$_6$ alkyl, C$_1$-C$_6$ alkoxy and cyano; and optionally and independently of each other substituted by one or more of halogen, amino, amido, guanidyl, hydroxyl, thiol, or carboxyl, and the benzyl group is optionally substituted by one or more of the halogen or hydroxyl groups, or R$_B$ and R$_C$ together with the carbon atom to which they are attached form a C$_3$-C$_6$ cycloalkyl group optionally substituted by one or more of halogen, amino, amido, guanidyl, hydroxyl, thiol, and carboxyl, and R$_D$ is hydrogen, (C$_1$-C$_6$) alkyl, (C$_2$-C$_6$) alkenyl, (C$_2$-C$_6$) alkynyl, or (C$_3$-C$_6$) cycloalkyl;

Y is selected from CH, CH$_2$, C(CH$_3$)$_2$ and CCH$_3$;

⸺ represents a single or double bond depending on Y; and

∼∼∼ represents the alpha or beta anomer depending on the position of R$_1$ or a compound of formula (Ia):

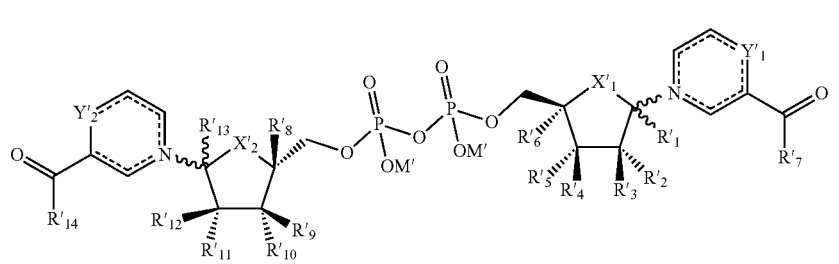

(Ia)

R$_A$ and R$_{A'}$ are independently selected from H, a C$_1$-C$_{10}$ alkyl, C$_2$-C$_{10}$ alkenyl, C$_2$-C$_{10}$ alkynyl, C$_3$-C$_{10}$ cycloalkyl, C$_1$-C$_{10}$ thioalkyl, C$_1$-C$_{10}$ hydroxylalkyl, C$_1$-C$_{10}$ alkyl aryl and C$_5$-C$_{12}$ aryl, C$_3$-C$_{10}$ heterocycloalkyl heteroaryl, —(CH$_2$)$_3$NHC(=NH)NH$_2$, (1H-indol-3-yl)methyl, (1H-imidazol-4-yl)methyl, and a side chain selected from a proteinogenic amino acid or a non-proteinogenic amino acid; wherein said aryl groups are optionally substituted with a group selected from hydroxyl, C$_1$-C$_{10}$ alkyl, C$_1$-C$_6$ alkoxy, halogen, nitro, and cyano; or R$_9$ and R$_{10}$ together with the phosphorus atoms to which they are attached form a 6-membered ring, wherein —R$_9$—R$_{10}$— represents CH$_2$—CH$_2$—CHR—; wherein R is selected from H, (C$_5$-C$_6$) aryl, and (C$_5$-C$_6$) heteroaryl, wherein said aryl or heteroaryl groups are optionally substituted with halogen, trifluoromethyl, C$_1$-C$_6$ alkyl, C$_1$-C$_6$ alkoxy and cyano; or R$_9$ and R$_{10}$ together with the phosphorus atoms to which they are attached form a 6-membered ring wherein -R$_9$-R$_{10}$— represents-O—CH$_2$—CH$_2$—CHR—O—; wherein R is selected from H, (C$_5$-C$_6$) aryl and (C$_5$-C$_6$) heteroaryl, wherein said aryl or heteroaryl groups are optionally substituted with halogen, trifluoromethyl, (C$_1$-C$_6$) alkyl, (C$_1$-C$_6$) alkoxy, and cyano;

R$_8$ is selected from H, OR, NHR$_{13}$, NR$_{13}$R$_{14}$, NH—NHR$_{13}$, SH, CN, N$_3$, and halogen;

wherein R$_{13}$ and R$_{14}$ are independently selected from H, (C$_1$-C$_8$) alkyl, (C$_1$-C$_8$) alkyl aryl, and —CR$_B$R$_C$—C(O)—OR$_D$, wherein R$_B$ and R$_C$ are independently hydrogen, (C$_1$-C$_6$) alkyl, (C$_1$-C$_6$) alkoxy, benzyl indolyl, or imidazolyl, wherein the (C$_1$-C$_6$) alkyl and the (C$_1$-C$_6$) alkoxy can be or a stereoisomer, salt, hydrate, solvate, or crystal thereof, wherein X'$_1$ and X'$_2$ are independently selected from O, CH$_2$, S, Se, CHF, CF$_2$, and C=CH$_2$;

R'$_1$ and R'$_{13}$ are independently selected from H, azido, cyano, C$_1$-C$_8$ alkyl, C$_1$-C$_8$ thioalkyl, C$_1$-C$_8$ heteroalkyl, and OR, wherein R is selected from H and C$_1$-C$_8$ alkyl, R'$_2$, R'$_3$, R'$_4$, R'$_5$, R'$_9$, R'$_{10}$, R'$_{11}$, and R'$_{12}$ are independently selected from H, halogen, azido, cyano, hydroxyl, C$_1$-C$_{12}$ alkyl, C$_1$-C$_{12}$ thioalkyl, C$_1$-C$_{12}$ heteroalkyl, C$_1$-C$_{12}$ haloalkyl, and OR, wherein R may be selected from H, C$_1$-C$_{12}$ alkyl, C(O)(C$_1$-C$_{12}$) alkyl, C(O)NH(C$_1$-C$_{12}$) alkyl, C(O)O (C$_1$-C$_{12}$) alkyl, C(O) aryl, C(O)(C$_1$-C$_{12}$) aryl, C(O)NH(C$_1$-C$_{12}$) aryl alkyl, C(O)O(C$_1$-C$_{12}$) aryl alkyl, or a C(O) CHR$_{AA}$NH$_2$ group, wherein R$_{AA}$ is a side chain selected from a proteinogenic amino acid;

R'$_6$ and R'$_8$ are independently selected from H, azido, cyano, C$_1$-C$_8$ alkyl, and OR, wherein R is selected from H and C$_1$-C$_8$alkyl;

R'$_7$ and R'$_{14}$ are independently selected from H, OR, NHR, NRR', NH—NHR, SH, CN, N$_3$, and halogen, wherein R and R' are independently selected from H and (C$_1$-C$_8$) aryl alkyl;

Y'$_1$ and Y'$_2$ are independently selected from CH, CH$_2$, C(CH$_3$)$_2$ or CCH$_3$;

M' is selected from H or a suitable counterion;

⸺ represents a single or double bond depending on Y'$_1$ and Y'$_2$; and ∼∼∼ represents an alpha or beta anomer depending on the position of R'$_1$ and R'$_{13}$;

and the combinations thereof.

Within the context of the invention, M' can be an internal or external counterion.

In a first preferred embodiment, the pharmaceutically acceptable derivative is the compound of formula (I).

In one variant of the first embodiment, X represents oxygen.

In one variant of the first embodiment, $R_1$ and $R_6$ each independently represent hydrogen.

In one variant of the first embodiment, $R_2$, $R_3$, $R_4$, and $R_5$ each independently represent hydrogen or OH.

In one variant of the first embodiment, Y represents CH.

In one variant of the first embodiment, Y represents $CH_2$.

In one variant of the first embodiment, $R_7$ represents hydrogen.

In one variant of the first embodiment, $R_7$ represents $P(O)(OH)_2$.

In one variant of the first embodiment,
X represents oxygen; and/or
$R_1$ and $R_6$ each independently represent hydrogen; and/or
$R_2$, $R_3$, $R_4$, and $R_5$ each independently represent hydrogen, or $R_2$, $R_3$, $R_4$, and $R_5$ independently represent OH; and/or
Y represents CH or $CH_2$; and/or
$R_7$ represents $P(O)R_9R_{10}$, wherein $R_9$ and $R_{10}$ are independently selected from OH, $OR_{11}$, $NHR_{13}$, $NR_{13}R_{14}$, $C_1$-$C_8$ alkyl, $C_2$-$C_8$ alkenyl, $C_2$-$C_8$ alkynyl, $C_3$-$C_{10}$ cycloalkyl, $C_5$-$C_{12}$ aryl, $C_1$-$C_8$ aryl alkyl, $C_1$-$C_8$ alkyl aryl, $C_1$-$C_8$ heteroalkyl, $C_1$-$C_8$ heterocycloalkyl, heteroaryl, and $NHCR_AR_AC(O)R12$.

In a particularly preferred variant of the first embodiment, the compound of the invention is selected from compounds of formulae I-B to I-J:

TABLE 1

| Compounds (anomers) | Structure |
|---|---|
| I-B (alpha) | 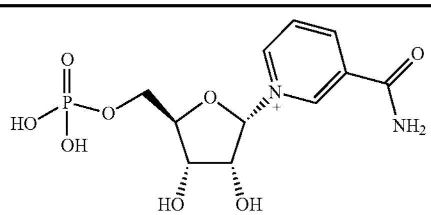 |
| I-C (beta) | 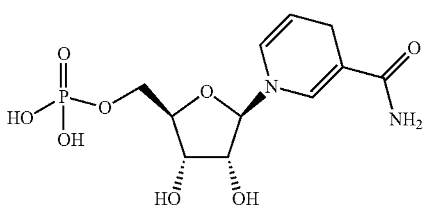 [SMILES: NC(=O)C1=CN([C@@H]2O[C@H](COP(=O)(O)O)[C@@H](O)[C@H]2O)C=CC1] |
| I-D (alpha) | 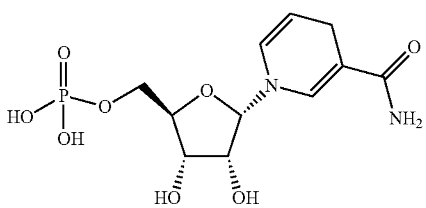 [SMILES: NC(=O)C1=CN([C@H]2O[C@H](COP(=O)(O)O)[C@@H](O)[C@H]2O)C=CC1] |
| I-E (beta) | 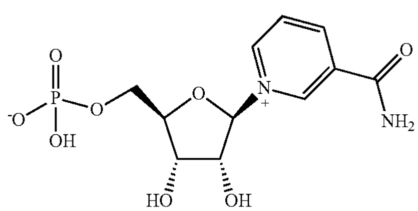 |

TABLE 1-continued

| Compounds (anomers) | Structure |
|---|---|
| I-F (alpha) | 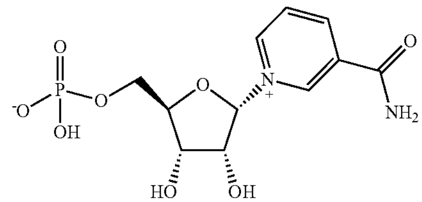 |
| I-G (beta) | 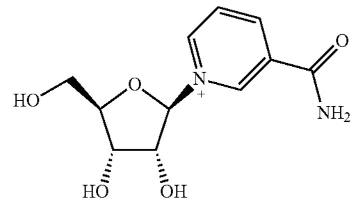 |
| I-H (alpha) | 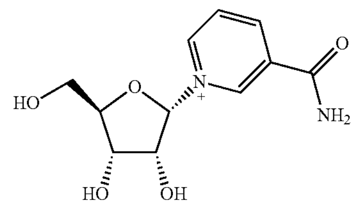 |
| I-I (beta) | 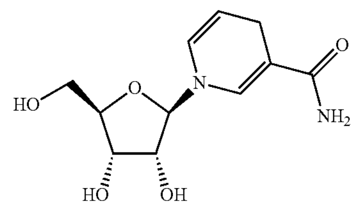 [SMILES: NC(=O)C1=CN([C@@H]2O[C@H](CO)[C@@H](O)[C@H]2O)C=CC1] |
| I-J (alpha) | 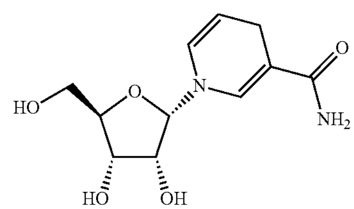 [SMILES: NC(=O)C1=CN([C@H]2O[C@H](CO)[C@@H](O)[C@H]2O)C=CC1] |

Advantageously, the pharmaceutically acceptable derivative of NMN can be alpha-NMN (compounds IB or I-F).

Advantageously, the pharmaceutically acceptable derivative of NMN may be dihydronicotinamide mononucleotide (NMN-H) (compounds IC or ID).

In a second preferred embodiment, the pharmaceutically acceptable derivative is the compound of formula (Ia).

In one variant of the second embodiment, $X'_1$ and $X'_2$ each independently represent oxygen.

In one variant of the second embodiment, $R'_7$ and $R'_{14}$ each independently represent $NH_2$.

In one variant of the second embodiment, $R'_1$ and/or $R'_{13}$ each independently represent hydrogen.

In one variant of the second embodiment, $R'_6$ and/or $R'_8$ each independently represent hydrogen.

In one variant of the second embodiment, $R'_2$, $R'_3$, $R'_4$, $R'_5$, $R'_9$, $R'_{10}$, $R'_{11}$, and $R'_{12}$ each independently represent hydrogen.

In one variant of the second embodiment, $R'_2$, $R'_3$, $R'_4$, $R'_5$, $R'_9$, $R'_{10}$, $R'_{11}$, and $R'_{12}$ each independently represent OH.

In one variant of the second embodiment, $Y'_1$ and $Y'_2$ each independently represent CH.

In one variant of the second embodiment, $Y'_1$ and $Y'_2$ each independently represent CH2.

In one variant of the second embodiment, the compound according to the invention is selected from compounds of formula Ia-A to Ia-I:

TABLE 2

| Compounds (anomers) | Structure |
|---|---|
| Ia-A (beta, beta) | 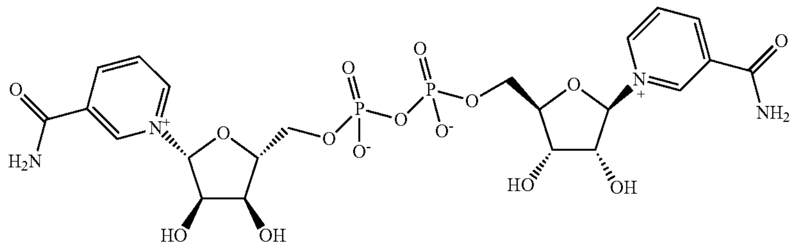 |
| Ia-B (beta, alpha) | 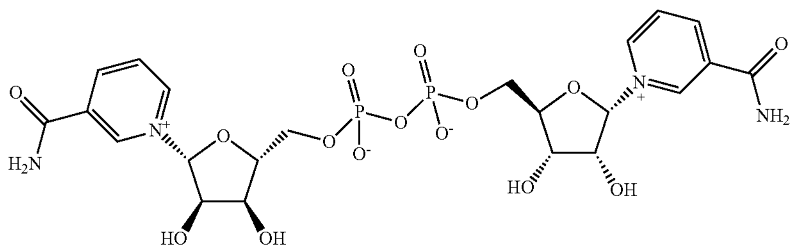 |
| Ia-C (alpha, alpha) | 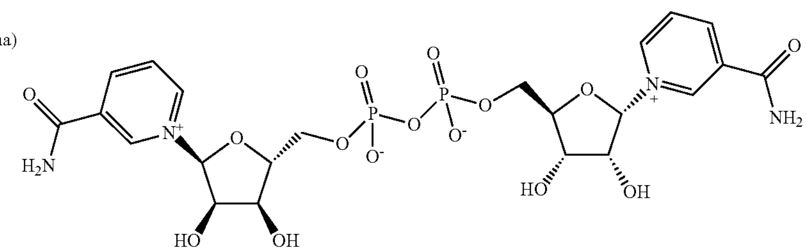 |
| Ia-D (beta, beta) | 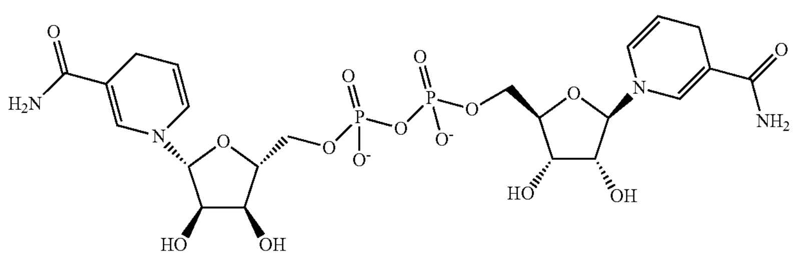 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| Ia-E (beta, alpha) | 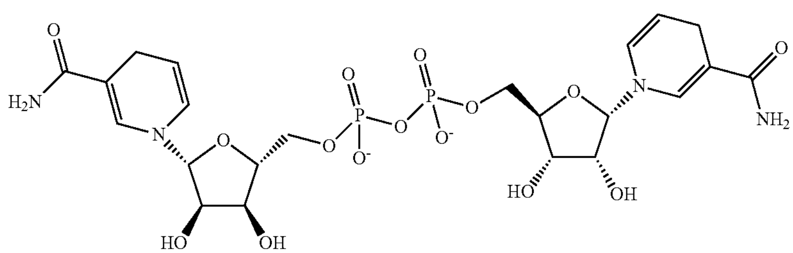 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |

TABLE 2-continued

| Compounds (anomers) | Structure |
|---|---|
| Ia-F (alpha, alpha) | [chemical structure] |
| Ia-G (beta, beta) | [chemical structure] |
| Ia-H (beta, alpha) | [chemical structure] |
| Ia-I (alpha, alpha) | [chemical structure] |

Preferably, the compound of formula Ia is selected from compounds of formula Ia-B, Ia-C, Ia-F, Ia-F, Ia-G, Ia-H and Ia-I, and combinations thereof.

Advantageously, NMN, a pharmaceutically acceptable derivative thereof, or a pharmaceutically acceptable salt thereof, can be used in treating and/or preventing joint pain induced by physical activity in mammals, preferably humans.

Advantageously, the joint pain relates to the neck, shoulder, scapula, elbow, wrist, hand joints, hip, sacroiliac joint, knee, ankle, foot joints, or combinations thereof.

Preferably, the joint pain relates to the knee.

Advantageously, the joint pain is not due to one of the pathologies selected from a tumor, arthritis, gout, osteoarthritis, joint deformation, connective tissue disease, dorsopathy, neurodegenerative disease, neuropathy, genetic disease, autoimmune disease, myopathy, osteopathy, osteoporosis, chondropathy, vasculopathy, viral infection, fungal infection, bacterial infection, parasite, side effect of medication, surgery, medical examination, calcification, trauma unless induced by physical activity, deformity, or combinations thereof.

Advantageously, the joint pain can be classified in one of the categories M22 to M25, preferably in category M25.5 of the International Classification of Diseases ICD-10.

In a preferred embodiment, the physical activity is playing a sport.

Advantageously, NMN, a pharmaceutically acceptable derivative thereof, or a pharmaceutically acceptable salt thereof, can be administered between 1 and 10 times per day, preferably between 1 and 5 times per day, more preferably between 1 and 3 times per day.

In a preferred embodiment, NMN, a pharmaceutically acceptable derivative thereof, or a pharmaceutically acceptable salt thereof, is administered twice daily.

Advantageously, NMN, a pharmaceutically acceptable derivative thereof, or a pharmaceutically acceptable salt thereof, may be used in combination with at least one other therapeutic agent.

Advantageously, the at least one therapeutic agent may be an analgesic, a non-steroidal anti-inflammatory, cortisone, a cortisone derivative, or combinations thereof.

Advantageously, the analgesic can be selected from paracetamol, nefopam, ketanin, tetrahydrocannabinol, cannabinoids, aspirin, methyl salicylate, diflunisal, salicylamide, codeine, alfentanil, carfentanil, dihydrocodeine, codeinone, tramadol, morphine, morphinone buprenorphine, fentanyl, acetyl fentanyl, remifentanil, sufentanil, heroin, hydromorphone, nalbuphine, oxycodone, hydroxycodone, oxymorphone, laudanum, methadone, pethidine, dextropropoxyphene, endorphin, tapentadol, thebaine, vicodin, and combinations thereof.

Advantageously, the non-steroidal anti-inflammatory drug can be selected from ibuprofen, ketoprofen, naproxen, ketorolac, alminoprofen, aceclofenac, mefenamic acid, niflumic acid, tiaprofenic acid, celecoxib rofecoxib, valdecoxib, parecoxib, dexketoprofen, diclofenac, etodolac, etoricoxib, fenoprofen, flurbiprofen, indomethacin, meloxicam, nabumetone, piroxicam, sulindac, tenoxicam, nimesulide, and combinations thereof.

Advantageously, the cortisone derivative can be selected from betamethasone, ciprofloxacin, cortivazol, dexamethasone, fludrocortisone, methylprednisolone, prednisolone, triamcinolone, and combinations thereof.

Advantageously, nicotinamide mononucleotide (NMN), a pharmaceutically acceptable derivative thereof, or a pharmaceutically acceptable salt thereof, reduces joint stiffness.

Advantageously, nicotinamide mononucleotide (NMN), a pharmaceutically acceptable derivative thereof, or a pharmaceutically acceptable salt thereof, improves joint function.

The present invention also relates to a composition comprising nicotinamide mononucleotide (NMN), a pharmaceutically acceptable derivative thereof, or a pharmaceutically acceptable salt thereof, and at least one pharmaceutically acceptable excipient for use in preventing and/or treating joint pain induced by physical activity, administered topically.

Advantageously, the composition according to the invention may be in the form of a gel, a solution, a water-in-oil emulsion, an oil-in-water emulsion, a cream, an ointment, or a liniment.

In a preferred embodiment, the composition according to the invention is in the form of a water-in-oil emulsion or an oil-in-water emulsion, more preferably an oil-in-water emulsion.

In a more preferred embodiment, the composition according to the invention is in the form of a hydrophilic or lipophilic gel, even more preferably in the form of a hydrophilic gel.

Advantageously, the composition according to the invention may be a pharmaceutical composition.

Advantageously, the composition according to the invention may comprise NMN, one of the salts thereof, or one of the pharmaceutically acceptable derivatives thereof, in an amount of between 0.05% and 15% by weight, preferably between 1 and 10% by weight, more preferably between 3 and 5% by weight relative to the total weight of the composition.

Advantageously, NMN, a pharmaceutically acceptable derivative thereof, or a pharmaceutically acceptable salt thereof, can be administered between 1 and 10 times per day, preferably between 1 and 5 times per day, more preferably between 1 and 3 times per day.

In a preferred embodiment, NMN, a pharmaceutically acceptable derivative thereof, or a pharmaceutically acceptable salt thereof, may be administered twice daily.

Advantageously, the composition according to the invention may further comprise at least one additional therapeutic agent as defined above for use in preventing and/or treating joint pain induced by physical activity as set out above.

Definitions

In the present invention, the following terms have the following meanings.

Unless otherwise specified, the nomenclature for substituents not explicitly defined in the present invention is obtained by naming the terminal portion of the functionality followed by the functionality adjacent to the point of attachment.

"Alkyl" by itself or as part of another substituent, refers to a hydrocarbyl radical of the formula $C_nH_{2n+1}$ wherein n is a number greater than or equal to 1. In general, the alkyl groups of this invention comprise from 1 to 12 carbon atoms, preferably from 1 to 8 carbon atoms, more preferably from 1 to 6 carbon atoms, even more preferably from 1 to 2 carbon atoms. Alkyl groups may be linear or branched and may be substituted as described in the present invention. Alkyls suitable for implementing the invention may be selected from methyl, ethyl, n-propyl, i-propyl, n-butyl, i-butyl, s-butyl and t-butyl, pentyl and the isomers thereof such as n-pentyl and iso-pentyl, and hexyl and the isomers thereof such as n-hexyl and iso-hexyl, heptyl and the isomers thereof (e.g., n-heptyl, iso-heptyl), octyl and the isomers thereof (e.g., n-octyl, iso-octyl), nonyl and the isomers thereof (e.g., n-nonyl, iso-nonyl), decyl and the isomers thereof (e.g., n-decyl, iso-decyl), undecyl and the isomers thereof, dodecyl and the isomers thereof. Preferably, the alkyl groups can be selected from methyl, ethyl, n-propyl, i-propyl, n-butyl, i-butyl, s-butyl, t-butyl, n-pentyl, n-hexyl, n-heptyl, n-octyl, n-nonyl and n-decyl. The saturated and branched alkyl groups may be selected from, but are not limited to, isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyle, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, and 3,3-diethylhexyl. Preferred alkyl groups are methyl, ethyl, n-propyl, i-propyl, n-butyl, i-butyl, s-butyl, and t-butyl. Cx-Cy-alkyl refers to alkyl groups that include x to y carbon atoms.

When the suffix "ene" ("alkylene") is used in conjunction with an alkyl group, it means that the alkyl group as defined herein has two single bonds as points of attachment to other groups. The term "alkylene" includes methylene, ethylene, methyl methylene, propylene, ethyl ethylene, and 1,2-dimethylethylene.

The term "alkenyl" as used herein refers to an unsaturated hydrocarbyl group, which may be linear or branched, comprising one or more carbon-carbon double bonds. Suitable alkenyl groups comprise between 2 and 12 carbon atoms, preferably between 2 and 8 carbon atoms, and even more preferably between 2 and 6 carbon atoms. Examples of alkenyl groups are ethenyl, 2-propenyl, 2-butenyl, 3-butenyl, 2-pentenyl and the isomers thereof, 2-hexenyl and the isomers thereof, 2,4-pentadienyl, and the like.

The term "alkynyl" as used herein refers to a class of monovalent unsaturated hydrocarbyl groups, in which the unsaturation results from the presence of one or more carbon-carbon triple bonds. Alkynyl groups generally, and preferably, have the same number of carbon atoms as described above for alkenyl groups. Non-limiting examples of alkynyl groups are ethynyl, 2-propynyl, 2-butynyl, 3-butynyl, 2-pentynyl and the isomers thereof, 2-hexynyl and the isomers thereof, etc.

"Alkoxy" means an alkyl group as defined above that is attached to another moiety through an oxygen atom. Examples of alkoxy groups include methoxy, isopropoxy, ethoxy, tert-butoxy, and others. Alkoxy groups may optionally be substituted with one or more substituents. The alkoxy groups included in the compounds of this invention may be optionally substituted with a solubilizing group.

"Aryl" as used herein refers to a polyunsaturated aromatic hydrocarbyl group having a single ring (e.g., phenyl) or a plurality of aromatic rings fused together (e.g., naphthyl) or covalently bonded, generally containing from 5 to 18 atoms, preferably from 5 to 12, more preferably from 6 to 10, of which at least one ring is aromatic. The aromatic ring may optionally include one or two additional rings (cycloalkyl, heterocyclyl, or heteroaryl) fused thereto. Aryl is also intended to include partially hydrogenated derivatives of the carbocyclic systems listed herein. Examples of aryl include phenyl, biphenylyl, biphenylenyl, 5- or 6-tetralinyl, naphthalene-1- or -2-yl, 4-, 5-, 6- or 7-indenyl, 1-2-, 3-, 4- or 5-acenaphthyl, 3-, 4- or 5-acenaphthyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

When at least one carbon atom in an aryl group is replaced by a heteroatom, the resulting ring is referred to herein as a "heteroaryl" ring.

"Alkyl aryl" means an aryl group substituted with an alkyl group.

"Amino acid" means an alpha-amino carboxylic acid, i.e., a molecule comprising a carboxylic acid functional group and an amine functional group at the alpha position of the carboxylic acid group, e.g., a proteinogenic amino acid or a non-proteinogenic amino acid. "Proteinogenic amino acid" refers to an amino acid that is incorporated into proteins during translation of messenger RNA by ribosomes in living organisms, i.e., alanine (ALA), arginine (ARG), asparagine (ASN), aspartate (ASP), cysteine (CYS), glutamate (glutamic acid) (GLU), glutamine (GLN), glycine (GLY), histidine (HIS), isoleucine (ILE), leucine (LEU), lysine (LYS), methionine (MET), phenylalanine (PHE), proline (PRO), pyrrolysine (PYL), selenocysteine (SEL), serine (SER), threonine (THR), tryptophan (TRP), tyrosine (TYR), or valine (VAL).

"Non-proteinogenic amino acid" as used herein refers to an amino acid that is not naturally encoded or found in the genetic code of a living organism. Non-limiting examples of a non-proteinogenic amino acid are ornithine, citrulline, argininosuccinate, homoserine, homocysteine, cysteine sulfinic acid, 2-aminomuconic acid, δ-aminolevulinic acid, β-alanine, cystathionine, γ-aminobutyrate, DOPA, 5-hydroxytryptophan, D-serine, ibotenic acid, α-aminobutyrate, 2-aminoisobutyrate, D-leucine, D-valine, D-alanine, or D-glutamate.

The term "cycloalkyl" as used herein is a cyclic alkyl group, i.e., a monovalent, saturated, or unsaturated hydrocarbyl group having 1 or 2 ring structures. The term "cycloalkyl" includes monocyclic or bicyclic hydrocarbyl groups. Cycloalkyl groups may comprise 3 or more carbon atoms in the ring and generally, according to the present invention, comprise from 3 to 10, more preferably from 3 to 8 carbon atoms and even more preferably from 3 to 6 carbon atoms. Examples of cycloalkyl groups include, but are not limited to, cyclopropyl, cyclobutyl, cyclopentyl, cyclohexyl, with cyclopropyl being particularly preferred.

"Pharmaceutically acceptable excipient" refers to an inert vehicle or carrier used as a solvent or diluent in which the active ingredient is formulated and/or administered, and which does not produce an adverse, allergic, or other reaction when administered to an animal, preferably a human. This includes all solvents, dispersion media, coatings, antibacterial and antifungal agents, isotonic agents, absorption retardants, and other similar ingredients. For human administration, preparations must meet standards of sterility, general safety and purity as required by regulatory agencies, such as, for example, the FDA or EMA. In the context of the invention, "pharmaceutically acceptable excipient" includes all pharmaceutically acceptable excipients as well as all pharmaceutically acceptable carriers, diluents, and/or adjuvants.

"Halogen" or "halo" means fluoro, chloro, bromo or iodo. The preferred halo groups are fluoro and chloro.

"Haloalkyl" alone or in combination means an alkyl radical having the meaning as defined above, in which one or more hydrogen atoms are replaced by a halogen as defined above. Examples of such haloalkyl radicals include chloromethyl, 1-bromoethyl, fluoromethyl, difluoromethyl, trifluoromethyl, 1,1,1-trifluoroethyl, and the like. Cx-Cy-haloalkyl and Cx-Cy-alkyl refer to alkyl groups that include from x to y carbon atoms. Preferred haloalkyl groups are difluoromethyl and trifluoromethyl.

"Heteroalkyl" means an alkyl group as defined above in which one or more carbon atoms are replaced by a heteroatom selected from oxygen, nitrogen, and sulfur atoms. In heteroalkyl groups, the heteroatoms are bonded along the alkyl chain only to carbon atoms, i.e., each heteroatom is separated from any other heteroatom by at least one carbon atom. However, the nitrogen and sulfur heteroatoms may optionally be oxidized, and the nitrogen heteroatoms may optionally be quaternized. A heteroalkyl is bonded to another group or molecule solely by a carbon atom, i.e., the linking atom is not selected from the heteroatoms included in the heteroalkyl group.

The term "heteroaryl" as used herein, alone or as part of another group, refers to, but is not limited to, aromatic rings of 5 to 12 carbon atoms or ring systems containing 1 or 2 rings that are fused or covalently bonded, typically containing 5 or 6 atoms; at least one of which is aromatic, wherein one or more carbon atoms in one or more of these rings are replaced by oxygen, nitrogen and/or sulfur atoms, wherein the nitrogen and sulfur heteroatoms may optionally be oxidized, and the nitrogen heteroatoms may optionally be quaternized. These rings may be fused to an aryl, cycloalkyl, heteroaryl or heterocyclyl ring. Non-limiting examples of such heteroaryls include furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo [2, 1-b] [1,3]thiazolyl, thieno [3,2-b] furanyl, thieno [3,2-b] thiophenyl, thieno [2,3-d] [1,3] thiazolyl, thieno [2,3-d]imidazolyl, tetrazolo [1,5-a] pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

When at least one carbon atom in a cycloalkyl group is replaced by a heteroatom, the resulting ring is referred to here as "heterocycloalkyl" or "heterocyclyl".

The terms "heterocyclyl," "heterocycloalkyl," or "heterocyclo," as used herein by themselves or as part of another group, refer to non-aromatic, fully saturated or partially unsaturated (e.g., 3- to 7-membered monocyclic, 7- to 11-membered bicyclic, or containing a total of 3 to 10 ring atoms) cyclic groups that have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, wherein the nitrogen and sulfur heteroatoms may optionally be oxidized, and the nitrogen heteroatoms may optionally be quaternized. Any of the carbon atoms of the heterocyclic group may be substituted with an oxo (e.g., piperidone, pyrrolidinone). The heterocyclic group may be attached to any heteroatom or carbon atom of the ring or ring system, where valence permits. The rings of multi-ring heterocycles may be fused, bridged, and/or connected by one or more spiro atoms. Exemplary non-limiting heterocyclic groups include oxetanyl, piperidinyl, azetidinyl, 2-imidazolinyl, pyrazolidinyl, imidazolidinyl, isoxazolinyl, oxazolidinyl, isoxazolidinyl, thiazolidinyl, isothiazolidinyl piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-yl sulfoxide, thiomorpholin-4-yl sulfone, 1,3-dioxolanyl, 1,4-oxathianyl, 1H-pyrrolizinyl, tetrahydro-1,1-dioxothiophenyl, N-formylpiperazinyl, and morpholin-4-yl.

The term "precursor" as used herein also refers to pharmacologically acceptable derivatives of compounds of formula (I) or (Ia) such as esters of which the in vivo biotransformation product is the active drug. Precursors are characterized by increased bioavailability and are readily metabolized to active compounds in vivo. Suitable precursors for the purposes of the invention include carboxylic esters, in particular alkyl esters, aryl esters, acyloxyalkyl esters, and carboxylic esters of dioxolene; ascorbic acid esters.

"Pharmaceutically acceptable" means approved or approvable by a regulatory agency or listed in a recognized pharmacopoeia for use in animals, and more preferably in humans. It may be a substance that is not biologically or otherwise undesirable, i.e., the substance can be administered to an individual without causing undesirable biological effects or deleterious interactions with any of the components of the composition in which it is contained. Preferably, a "pharmaceutically acceptable" salt or excipient means any salt or excipient authorized by the European Pharmacopoeia (noted as "Ph. Eur.") and the United States Pharmacopeia (noted as "USP").

The term "active ingredient" or "therapeutic agent" refers to a molecule or substance, the administration of which to a subject slows or stops the progression, worsening, or deterioration of one or more symptoms of a disease or condition; relieves the symptoms of a disease or condition; cures a disease or condition. According to one embodiment, the therapeutic ingredient is a small molecule, natural or synthetic. According to another embodiment, the therapeutic ingredient is a biological molecule such as, for example, an oligonucleotide, siRNA, miRNA, DNA fragment, aptamer, antibody, and the like. "Pharmaceutically acceptable salts" include acid addition and base addition salts of such salts. Suitable acid addition salts are formed from acids that form non-toxic salts. Examples include acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, and xinofoate salts. Suitable basic salts are formed from bases that form non-toxic salts. Examples include aluminum, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine, and zinc salts. Hemisalts of acids and bases can also be formed, for example, hemisulfates and salts of chemical calcium. Preferred pharmaceutically acceptable salts are hydrochloride/chloride, bromide/hydrobromide, bisulfate/sulfate, nitrate, citrate, and acetate.

Pharmaceutically acceptable salts can be prepared by one or more of these methods:
  by reacting the compound with the desired acid;
  by reacting the compound with the desired base;
  removing an acid or base labile protecting group from a suitable precursor of the compound or ring opening a suitable cyclic precursor, e.g., a lactone or lactam, using the desired acid; or
  by converting one salt of the compound into another by reaction with a suitable acid or by means of a suitable ion exchange column.

All of these reactions are usually performed in solution. The salt may precipitate out of solution and be collected by filtration or may be recovered by evaporating the solvent. The degree of ionization of the salt can vary from fully ionized to nearly un-ionized.

"Solvate" is used herein to describe a molecular complex comprising the compound of the invention and one or more pharmaceutically acceptable solvent molecules, for example, ethanol.

The term "substituent" or "substituted" means that a hydrogen radical on a compound or group is replaced with any desired group that is substantially stable under the conditions of the reaction in an unprotected form or when protected by a protecting group. Examples of preferred substituents include, but are not limited to, halogen (chloro, iodo, bromo or fluoro); alkyl; alkenyl; alkynyl, as described above; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or polycyclic fused or unfused (e.g., cyclopropyl, cyclobutyl, cyclopentyl or cyclohexyl), or heterocycloalkyl, which may be monocyclic or polycyclic fused or unfused (e.g., pyrrolidinyl, piperidinyl, piperazinyl, morpholinyl, or thiazinyl), monocyclic or polycyclic fused or unfused, aryl or heteroaryl (for example, aryl, heteroaryl, pyrrolidinyl, piperidinyl, piperazinyl, morpholinyl or thiazinyl), monocyclic or polycyclic fused or unfused (e.g., aryl, heteroaryl, pyrrolidinyl, piperidinyl, piperazinyl, morpholinyl or thiazinyl), phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary or tertiary); $CO_2CH_3$; $CONH2$; $OCH_2CONH_2$; $NH_2$; $SO_2NH_2$; $OCHF_2$; $CF_3$; $OCF_3$; and these moieties may also be optionally substituted with a fused ring structure or bridge, e.g., —$OCH_2O$—. These substituents may optionally be further substituted with a substituent selected from these groups. In some embodiments, the term "substituent" or the adjective "substituted" refers to a substituent selected from the group consisting of alkyl, alkenyl, alkynyl, cycloalkyl, cycloalkenyl, heterocycloalkyl, aryl, heteroaryl, arylalkyl, heteroarylalkyl, haloalkyl, —$C(O)NR_{11}R_{12}$, —$NR_{13}C(O)R_{14}$, halo, —$OR_{13}$, cyano, nitro, haloalkoxy, —$C(O)R_{13}$, —$NR_{11}R_{12}$, —$SR_{13}$, $C(O)OR'_{13}$, —$OC(O)R_{13}$, —$NR_{13}C(O)NR_{11}R_{12}$, —$OC(O)NR_{11}R_{12}$, —$NR_{13}C(O)OR_{14}$, —$S(O)rR13$, —$NR_{13}S(O)rR_{14}$, —$OS(O)rR_{14}$, $S(O)rNR_{11}R_{12}$, —$O$, —$S$, and —$N$—$R_{13}$, where r is 1 or 2; $R_{11}$ and $R_{12}$, for each occurrence, are, independently, H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, or optionally substituted heteroarylalkyl; or $R_{11}$ and $R_{12}$ taken together with the nitrogen to which they are attached are optionally substituted heterocycloalkyl or optionally substituted heteroaryl; and $R_{13}$ and $R_{14}$ for each occurrence are, independently, H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, or optionally substituted heteroarylalkyl. In some embodiments, the term "substituent" or the adjective "substituted" refers to a solubilizing group.

The term "administration", or a variation thereof (e.g., "administer"), means to provide the active ingredient, alone or as part of a pharmaceutically acceptable composition, to the patient in whom the condition, symptom, or disease is to be treated or prevented.

"Treat," "cure," and "treatment," as used in the present invention, are intended to include the relief, alleviation, or removal of a condition or disease and/or the associated symptoms thereof.

"Prevent," "prevent," and "prevention," as used in this invention, refer to a method for delaying or preventing the onset of a condition or disease and/or the associated symptoms thereof, preventing a patient from contracting a condition or disease, or reducing the risk of a patient contracting a condition or disease.

The bonds of an asymmetric carbon may be represented herein using a solid triangle ( ▬▬ ), a dotted triangle ( ····· ) or a zigzag line ( ∿∿∿ ).

DETAILED DESCRIPTION OF THE INVENTION

The present invention relates to nicotinamide mononucleotide (NMN), a pharmaceutically acceptable derivative thereof, or a pharmaceutically acceptable salt thereof, for topical use in preventing and/or treating joint pain induced by physical activity, and compositions comprising same.

Nicotinamide adenine dinucleotide (NAD) is a coenzyme present in all living cells. NAD exists in the cell either in the oxidized form thereof NAD+ or in the reduced form thereof NADH. The role of NAD is that of an electron carrier involved in the redox reactions of metabolism. NAD is also involved in many cellular processes such as the ribosylation of ADP as part of post-translational modifications of proteins.

NAD can be synthesized de novo by the cell from amino acids such as tryptophan or aspartate. However, this synthesis is marginal because the main pathway for NAD synthesis is the salvage pathway whereby the cell, and primarily the cell nucleus, recycles compounds to reform NAD from precursors. NAD precursors include niacin, nicotinamide riboside, nicotinamide mononucleotide, and nicotinamide.

NMN is one of the compounds allowing the synthesis of NAD by the salvage route and has the formula:

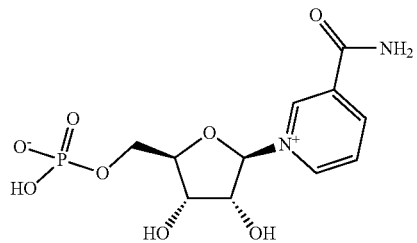 [SMILES: NC(=O)c1ccc[n+]([C@@H]2O[C@H](COP(=O)([O-])O)[C@@H](O)[C@H]2O)c1]

The inventors have demonstrated that the use of NMN, the pharmaceutically acceptable salts and/or derivatives thereof, and the composition according to the invention makes it possible to relieve joint pain resulting from physical activity, and in particular from playing sports. Preferably, the joint pain is gonalgia, i.e., a pain felt in the knee.

The inventors have demonstrated that the use of NMN, one of the pharmaceutically acceptable derivatives thereof, or one of the pharmaceutically acceptable salts thereof, as well as compositions comprising same, is particularly effective in reducing joint pain, in particular gonalgia, induced by physical activity, in particular sports activities. More precisely, the inventors have demonstrated that the use of NMN, one of the pharmaceutically acceptable derivatives thereof, or one of the pharmaceutically acceptable salts thereof, as well as the compositions comprising same, reduces joint pain, in particular gonalgia, effectively enough to avoid the use of conventional therapies.

According to the WHO, physical activity is any movement produced by skeletal muscles, responsible for an increase in energy expenditure. Physical activity can be linked to professional activity. Leisure-time physical activities can include sports but also activities performed without supervision: for example, walking, cycling, scootering, in parks and green spaces, in the countryside; specialized facilities with free access can be used to perform physical activities (fitness tracks, multi-sports fields, outdoor fitness areas, bicycle paths, hiking trails . . . ). Domestic activities involve physical activities performed at home, inside or outside (going up and down stairs, housework—vacuuming, carrying groceries—, DIY, gardening). Finally, in a preferred embodiment, the invention applies to joint pains resulting from playing sports.

According to the WHO, playing sports or "exercising" is a more deliberate, structured, repetitive subcategory of physical activity aimed at improving or maintaining one or more aspects of physical fitness. In the context of the present invention, the term "exercise" is used interchangeably with "sport" and "sports activity". According to ANSES, sport can also be defined as a physical activity where participants adhere to a common set of rules and where a performance objective is defined (for example: team sports, gymnastics, water gymnastics, running, Nordic walking, cycling, cross-country skiing, rowing, swimming).

Global recommendations relating to physical activity for health are formulated by the WHO, taking into account the age of the target population and the intensity of the physical activity. For example, the WHO physical activity guidelines recommend that children and adolescents aged 5 to 17 years should engage in at least 60 minutes of moderate to vigorous physical activity daily, with the understanding that more than 60 minutes of physical activity per day will provide additional health benefits, and should include muscle- and bone-strengthening activities at least three times per week. According to the WHO physical activity recommendations, adults aged 18-64 should engage in at least 150 minutes of moderate-intensity physical activity per week, or at least 75 minutes of vigorous physical activity per week, or an equivalent combination of moderate- and vigorous-intensity physical activity. For additional health benefits, adults should increase their moderate-intensity physical activity to 300 minutes per week or the equivalent, and should also engage in muscle-strengthening activities involving major muscle groups two or more days per week. According to the WHO physical activity recommendations, adults aged 65 years and older should engage in 150 minutes of moderate-intensity physical activity per week, or at least 75 minutes of vigorous physical activity per week, or an equivalent combination of moderate- and vigorous-intensity physical activity. For additional health benefits, they should increase their moderate-intensity physical activity to 300 minutes per week, or the equivalent. People with mobility impairments should engage in physical activity to improve balance and prevent falls three or more days per week. Muscle-strengthening activities involving major muscle groups should be done twice a week or more.

In addition, the use of NMN, a molecule naturally present in the body, has many advantages. In particular, NMN does not pose any tolerance problems for patients. The use of NMN and the composition according to the invention does not induce any allergy. Moreover, the use of NMN and the composition according to the invention does not cause the side effects frequently encountered with conventional treatments.

In particular, NMN does not induce any physical or psychological dependence, unlike analgesics containing morphine or opium derivatives. Moreover, NMN does not induce any bone fragility or vulnerability to infections as observed with chronic administration of cortisone or the derivatives thereof. The use of NMN and the composition according to the invention to prevent and/or treat joint pain such as gonalgia resulting from physical activity, and in particular playing sports, is therefore safe for patients.

NMN and the composition according to the invention can also be used in children and adults. NMN is indeed well tolerated by children. In the context of the invention, a patient is considered to be a child when his or her age is less than 18 years and an adult from the age of 18 years. Therefore, the invention is also of interest for treating gonalgia in children.

In a particularly preferred embodiment, the NMN is in the form of a zwitterion. A "zwitterion" is defined as a molecular chemical species having electrical charges of opposite sign and located, in general, on non-adjacent atoms in the molecule.

The pharmaceutically acceptable NMN derivative may be selected from a compound of formula (I):

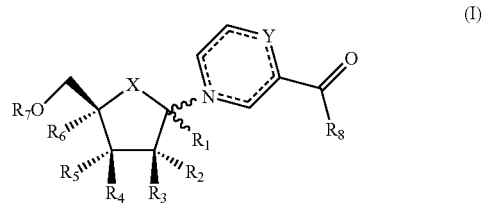

or a stereoisomer, salt, hydrate, solvate, or pharmaceutically acceptable crystal thereof, wherein:

X is selected from O, $CH_2$, S, Se, CHF, $CF_2$, and C=$CH_2$;

$R_1$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$ alkyl;

$R_2$, $R_3$, $R_4$, and $R_5$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR; wherein R is selected from H, $C_1$-$C_{12}$ alkyl, C(O)($C_1$-$C_{12}$)alkyl, C(O)NH($C_1$-$C_{12}$)alkyl, C(O)O($C_1$-$C_{12}$)alkyl, C(O)aryl, C(O)($C_1$-$C_{12}$)aryl alkyl, C(O)NH($C_1$-$C_{12}$)aryl alkyl, C(O)O($C_1$-$C_{12}$)aryl alkyl, and C(O)CHR$_{AA}$NH$_2$; wherein R$_{AA}$ is a side chain selected from a proteinogenic amino acid;

$R_6$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$alkyl;

$R_7$ is selected from H, P(O)$R_9R_{10}$, and P(S)$R_9R_{10}$ and

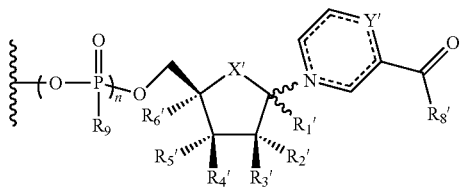

where n is an integer selected from 1, 2, or 3; wherein $R_9$ and $R_{10}$ are independently selected from OH, O$R_{11}$, NH$R_{13}$, N$R_{13}R_{14}$, $C_1$-$C_8$ alkyl, $C_2$-$C_8$ alkenyl, $C_2$-$C_8$ alkynyl, $C_3$-$C_{10}$ cycloalkyl, $C_5$-$C_{12}$, aryl ($C_1$-$C_8$)aryl alkyl, ($C_1$-$C_8$)aryl alkyl, ($C_1$-$C_8$) heteroalkyl, ($C_1$-$C_8$) heterocycloalkyl, heteroaryl and NHCHR$_A$R$_A$C(O)$R_{12}$; wherein:

$R_{11}$ is selected from $C_1$-$C_{10}$ alkyl, $C_3$-$C_{10}$ cycloalkyl, $C_5$-$C_{15}$ aryl, $C_1$-$C_{10}$ alkyl aryl, $C_5$-$C_{12}$ substituted aryl, $C_1$-$C_{10}$ heteroalkyl, $C_3$-$C_{10}$ heterocycloalkyl, $C_1$-$C_{10}$ haloalkyl, heteroaryl, —(CH$_2$)$_n$ C(O)($C_1$-$C_{15}$)alkyl, —(CH$_2$)$_n$ OC(O)($C_1$-$C_{15}$)alkyl, —(CH$_2$)$_n$ OC(O)O($C_1$-$C_{15}$)alkyl, —(CH$_2$)$_n$ SC(O)($C_1$-$C_{15}$)alkyl, —(CH$_2$)$_n$ C(O)O($C_1$-$C_{15}$)alkyl, and —(CH$_2$)$_n$ C(O)O($C_1$-$C_{15}$)alkyl aryl; wherein n is an integer selected from 1 to 8; P(O)(OH)OP(O)(OH)$_2$; halogen, nitro, cyano, $C_1$-$C_6$ alkoxy, $C_1$-$C_6$ haloalkoxy, —N($R_{11a}$)$_2$, $C_1$-$C_6$ acylamino, —COR$_{11b}$, —OCOR$_{11b}$; NHSO$_2$ ($C_1$-$C_6$ alkyl), —SO$_2$N($R_{11a}$)$_2$SO$_2$, wherein each of $R_{11a}$ is independently selected from H and $C_1$-$C_6$ alkyl and $R_{11b}$ is independently selected from OH, $C_1$-$C_6$ alkoxy, NH$_2$, NH($C_1$-$C_6$ alkyl)$_2$;

$R_{12}$ is selected from H, $C_1$-$C_{10}$ alkyl, $C_2$-$C_8$ alkenyl, $C_2$-$C_8$ alkynyl, $C_1$-$C_{10}$ haloalkyl, $C_3$-$C_{10}$ cycloalkyl, $C_3$-$C_{10}$ heterocycloalkyl, $C_5$-$C_{18}$ aryl, $C_1$-$C_4$ alkyl aryl, and $C_5$-$C_{12}$ heteroaryl; wherein said aryl or heteroaryl groups are optionally substituted with one or two groups selected from halogen, trifluoromethyl, $C_1$-$C_6$ alkyl, $C_1$-$C_6$ alkoxy, and cyano; and $R_4$ and $R_{4'}$ are independently selected from H, a $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ thioalkyl, $C_1$-$C_{10}$ hydroxylalkyl, $C_1$-$C_{10}$ alkyl aryl, and $C_5$-$C_{12}$ aryl, $C_3$-$C_{10}$ heterocycloalkyl heteroaryl, —$(CH_2)_3$NHC(=NH)NH$_2$, (1H-indol-3-yl)methyl, (1H-imidazol-4-yl)methyl, and a side chain selected from a proteinogenic amino acid or a non-proteinogenic amino acid; wherein said aryl groups are optionally substituted with a group selected from hydroxyl, $C_1$-$C_{10}$ alkyl, $C_1$-$C_6$ alkoxy, halogen, nitro, and cyano; or $R_9$ and $R_{10}$ together with the phosphorus atoms to which they are attached form a 6-membered ring, wherein —$R_9$—$R_{10}$— represents $CH_2$—$CH_2$—CHR—; wherein R is selected from H, ($C_5$-$C_6$) aryl and ($C_5$-$C_6$) heteroaryl, wherein said aryl or heteroaryl groups are optionally substituted with halogen, trifluoromethyl, $C_1$-$C_6$ alkyl, $C_1$-$C_6$ alkoxy, and cyano; or $R_9$ and $R_{10}$ together with the phosphorus atoms to which they are attached form a 6-membered ring wherein —$R_9$—$R_{10}$— represents —O—$CH_2$—$CH_2$—CHR—O—; wherein R is selected from H, ($C_5$-$C_6$) aryl, and ($C_5$-$C_6$) heteroaryl, wherein said aryl or heteroaryl groups are optionally substituted with halogen, trifluoromethyl, ($C_1$-$C_6$) alkyl, ($C_1$-$C_6$) alkoxy, and cyano;

$R_8$ is selected from H, OR, NHR$_{13}$, NR$_{13}$R$_{14}$, NH—NHR$_{13}$, SH, CN, N$_3$, and halogen; wherein R$_{13}$ and R$_{14}$ are independently selected from H, ($C_1$-$C_8$) alkyl, ($C_1$-$C_8$) alkyl aryl, and —CR$_B$R$_C$—C(O)—OR$_D$, wherein R$_B$ and R$_C$ are independently hydrogen, ($C_1$-$C_6$) alkyl, ($C_1$-$C_6$) alkoxy, benzyl indolyl or imidazolyl, wherein the ($C_1$-$C_6$) alkyl and the ($C_1$-$C_6$) alkoxy can be optionally and independently of each other substituted by one or more of halogen, amino, amido, guanidyl, hydroxyl, thiol, or carboxyl, and the benzyl group is optionally substituted by one or more of the halogen or hydroxyl groups, or R$_B$ and R$_C$ together with the carbon atom to which they are attached form a $C_3$-$C_6$ cycloalkyl group optionally substituted by one or more of the halogen, amino, amido, guanidyl, hydroxyl, thiol, and carboxyl groups, and R$_D$ is hydrogen, ($C_1$-$C_6$) alkyl, ($C_2$-$C_6$) alkenyl, ($C_2$-$C_6$) alkynyl, or ($C_3$-$C_6$) cycloalkyl;

Y is selected from CH, $CH_2$, $C(CH_3)_2$, and $CCH_3$;

⁓ represents a single or double bond depending on Y; and

⁓ represents the alpha or beta anomer depending on the position of $R_1$ or a compound of formula (Ia):

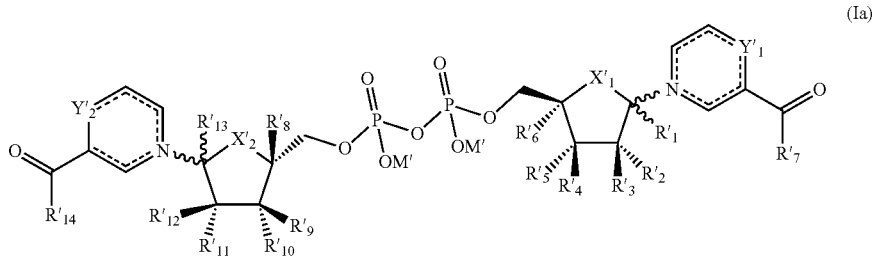

(Ia)

or a stereoisomer, salt, hydrate, solvate, or crystal thereof, wherein $X'_1$ and $X'_2$ are independently selected from O, $CH_2$, S, Se, CHF, $CF_2$, and C=$CH_2$;

$R'_1$ and $R'_{13}$ are independently selected from H, azido, cyano, $C_1$-$C_8$ alkyl, $C_1$-$C_8$ thioalkyl, $C_1$-$C_8$ heteroalkyl, and OR, wherein R is selected from H and $C_1$-$C_8$ alkyl, $R'_2$, $R'_3$, $R'_4$, $R'_5$, $R'_9$, $R'_{10}$, $R'_{11}$, $R'_{12}$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR, wherein R may be selected from H, $C_1$-$C_{12}$ alkyl, C(O)($C_1$-$C_{12}$) alkyl, C(O)NH($C_1$-$C_{12}$) alkyl, C(O)O ($C_1$-$C_{12}$) alkyl, C(O) aryl, C(O)($C_1$-$C_{12}$) aryl, C(O)NH($C_1$-$C_{12}$) aryl alkyl, C(O)O($C_1$-$C_{12}$) aryl alkyl, or a C(O) CHR$_{AA}$NH2 group, wherein R$_{AA}$ is a side chain selected from a proteinogenic amino acid;

$R'_6$ and $R'_8$ are independently selected from H, azido, cyano, $C_1$-$C_8$ alkyl, and OR, wherein R is selected from H and $C_1$-$C_8$ alkyl;

$R'_7$ and $R'_{14}$ are independently selected from H, OR, NHR, NRR', NH—NHR, SH, CN, N$_3$, and halogen, wherein R and R' are independently selected from H and ($C_1$-$C_8$) aryl alkyl;

$Y'_1$ and $Y'_2$ are independently selected from CH, $CH_2$, $C(CH_3)_2$, or $CCH_3$;

M' is selected from H or a suitable counterion;

⁓ represents a single or double bond depending on $Y'_1$ and $Y'_2$; and ⁓ represents an alpha or beta anomer depending on the position of $R'_1$ and $R'_{13}$;

and combinations thereof.

In the context of the invention, M' can be an internal or external counterion.

In a first preferred embodiment, the pharmaceutically acceptable derivative is the compound of formula (I).

In one variant of the first embodiment, X represents oxygen.

In one variant of the first embodiment, $R_1$ and $R_6$ each independently represent hydrogen.

In one variant of the first embodiment, $R_2$, $R_3$, $R_4$ and $R_5$ are each independently hydrogen or OH.

In one variant of the first embodiment, Y represents a CH.

In one variant of the first embodiment, Y represents a $CH_2$.

In one variant of the first embodiment, $R_7$ represents hydrogen.

In one variant of the first embodiment, $R_7$ represents P(O)(OH)$_2$.

In one variant of the first embodiment,

X represents oxygen; and/or $R_1$ and $R_6$ each independently represent hydrogen; and/or $R_2$, $R_3$, $R_4$ and $R_5$ each independently represent hydrogen or
$R_2$, $R_3$, $R_4$ and $R_5$ independently represent OH; and/or
Y represents CH or $CH_2$; and/or
$R_7$ represents $P(O)R_9$ and $R_{10}$, wherein $R_9$ and $R_{10}$ are independently selected from OH, $OR_{11}$, $NHR_{13}$, $NR_{13}R_{14}$, $C_1$-$C_8$ alkyl, $C_2$-$C_8$ alkenyl, $C_2$-$C_8$ alkynyl, $C_3$-$C_{10}$ cycloalkyl, $C_5$-$C_{12}$ aryl, $C_1$-$C_8$ aryl alkyl, $C_1$-$C_8$ alkyl aryl, $C_1$-$C_8$ heteroalkyl, $C_1$-$C_8$ heterocycloalkyl, heteroaryl, and $NHCR_4R_4C(O)R_{12}$.

In a particularly preferred embodiment of the first embodiment, the compound of the invention is selected from compounds of formulae I-B to I-J:

TABLE 1

| Compounds (anomers) | Structure |
|---|---|
| I-B (alpha) | 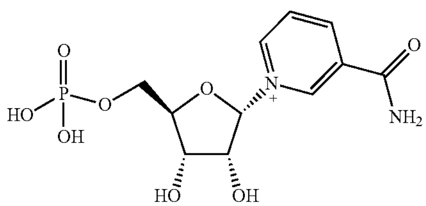 |
| I-C (beta) | 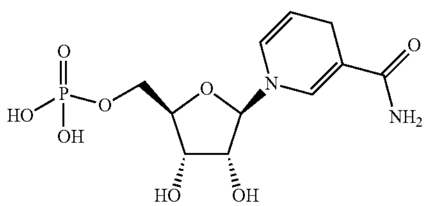 [SMILES: NC(=O)C1=CN([C@@H]2O[C@H](COP(=O)(O)O)[C@@H](O)[C@H]2O)C=CC1] |
| I-D (alpha) | 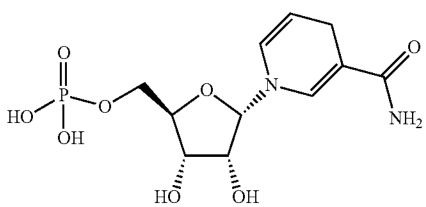 [SMILES: NC(=O)C1=CN([C@H]2O[C@H](COP(=O)(O)O)[C@@H](O)[C@H]2O)C=CC1] |
| I-E (beta) | 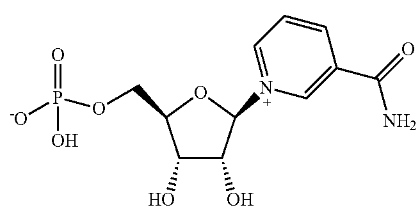 |
| I-F (alpha) | 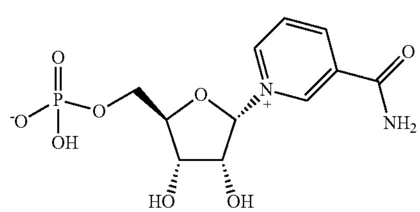 |
| I-G (beta) | 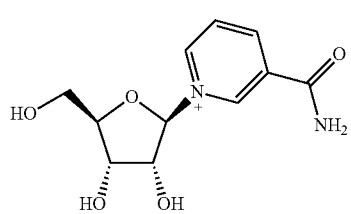 |

TABLE 1-continued

| Compounds (anomers) | Structure |
|---|---|
| I-H (alpha) | 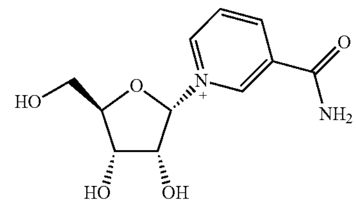 |
| I-I (beta) | 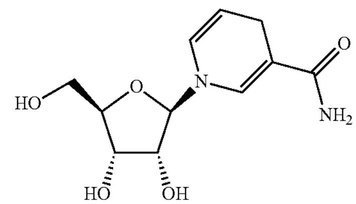 [SMILES: NC(=O)C1=CN([C@@H]2O[C@H](CO)[C@@H](O)[C@H]2O)C=CC1] |
| I-J (alpha) | 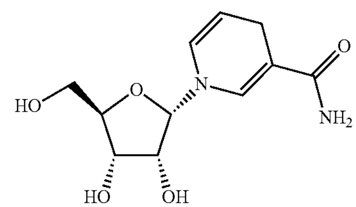 [SMILES: NC(=O)C1=CN([C@H]2O[C@H](CO)[C@@H](O)[C@H]2O)C=CC1] |

The pharmaceutically acceptable NMN derivative may be alpha-NMN (compounds I-B or I-F) or dihydronicotinamide mononucleotide (NMN-H) (compounds I-D or I-C) and combinations thereof.

In a second preferred embodiment, the pharmaceutically acceptable derivative is the compound of formula (Ia).

In one variant of the second embodiment, $X'_1$ and $X'_2$ each independently represent oxygen.

In one variant of the second embodiment, $R'_7$ and $R'_{14}$ each independently represent $NH_2$.

In one variant of the second embodiment, $R'_1$ and/or $R'_{13}$ each independently represent hydrogen.

In one variant of the second embodiment, $R'_6$ and/or $R'_8$ each independently represent hydrogen.

In one variant of the second embodiment, $R'_2$, $R'_3$, $R'_4$, $R'_5$, $R'_9$, $R'_{10}$, $R'_{11}$, and $R'_{12}$ each independently represent hydrogen.

In one variant of the second embodiment, $R'_2$, $R'_3$, $R'_4$, $R'_5$, $R'_9$, $R'_{10}$, $R'_{11}$, and $R'_{12}$ each independently represent OH.

In one variant of the second embodiment, $Y'_1$ and $Y'_2$ each independently represent CH.

In one variant of the second embodiment, $Y'_1$ and $Y'_2$ each independently represent $CH_2$.

In one variant of the second embodiment, the compound according to the invention is selected from compounds of formula Ia-A to Ia-I:

TABLE 2

| Compounds (anomers) | Structure |
|---|---|
| Ia-A (beta, beta) | 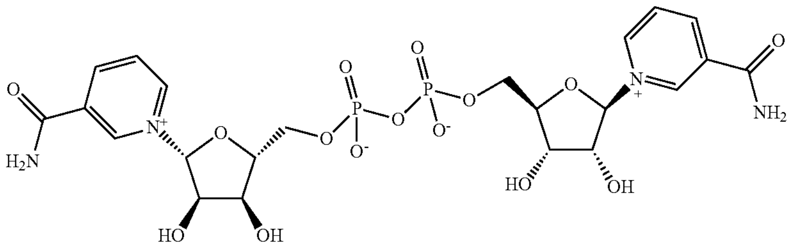 |
| Ia-B (beta, alpha) | 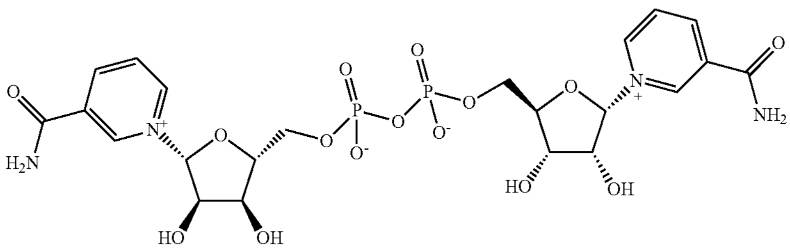 |
| Ia-C (alpha, alpha) | 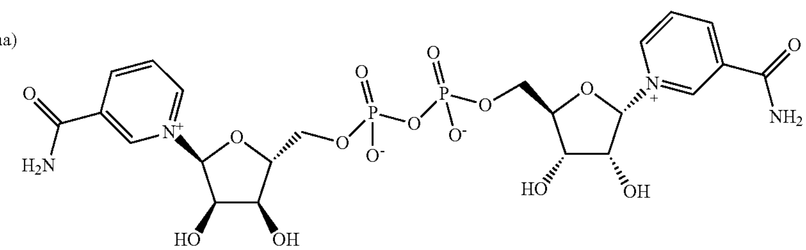 |
| Ia-D (beta, beta) | 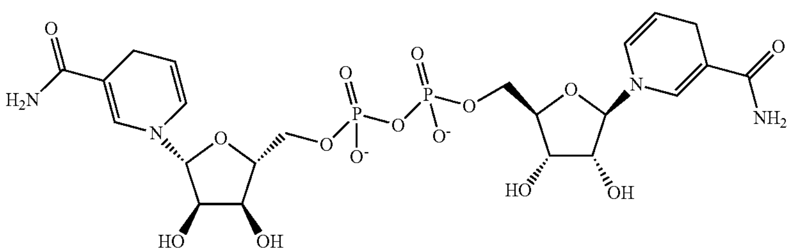 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| Ia-E (beta, alpha) | 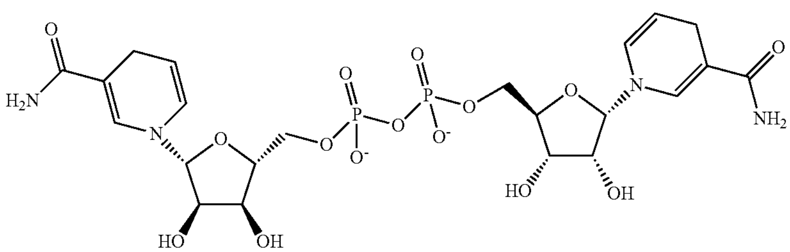 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| Ia-F (alpha, alpha) | 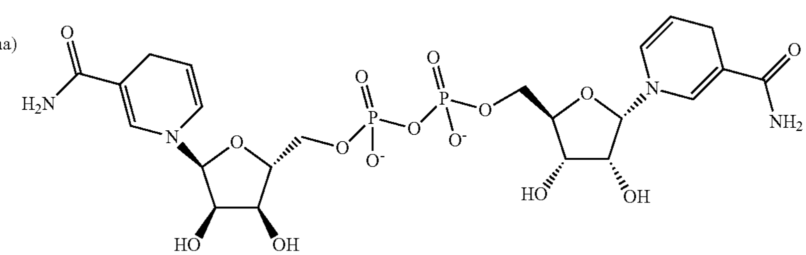 |

TABLE 2-continued

| Compounds (anomers) | Structure |
|---|---|
| Ia-G (beta, beta) | [chemical structure] |
| Ia-H (beta, alpha) | [chemical structure] |
| Ia-I (alpha, alpha) | [chemical structure] |

Preferably, the compound of formula Ia is selected from Ia-B, Ia-C, Ia-E, Ia-F, Ia-G, Ia-H, and Ia-I and combinations thereof.

NMN, one of the pharmaceutically acceptable derivatives thereof, or one of the pharmaceutically acceptable salts thereof, as well as compositions comprising same according to the invention can be used firstly to treat joint pain induced by physical activity, in particular playing sports.

By reducing the use of conventionally used therapies, or even replacing them, the present invention thus makes it possible to avoid, or at least reduce, the use of conventional treatments for joint pain and thus to avoid, or at least reduce, the occurrence of side effects associated with said therapies.

In the context of the present invention, joint pain results solely from physical activity, preferably from playing sports. Such pain is localized or diffuse and does not require surgical intervention to be cured. In particular, such pain may result from excessive physical activity, especially sports. It can also result from a wrong movement or improper equipment during a physical activity, and in particular while playing sports.

The joint pain may be classified in one of categories M22 to M25, preferably in category M25.5 of the International Classification of Diseases ICD-10. In other words, the joint pain may be classified in one of the categories M22, M23, M24 or M25, preferably in category M25.5 of the ICD-10 International Classification of Diseases.

However, in the context of the present invention, the joint pain is not due to any of the conditions selected from tumor, arthritis (ICD-10 classes M00 to M09 and M11 to M14), gout (ICD-10 class M10), osteoarthritis (ICD-10 classes M15 to M19), joint deformity (ICD-10 classes M20 and M21), connective tissue disease (ICD-10 classes M30 to M36), dorsopathy (ICD-10 classes M40 to M54), neurodegenerative disease, neuropathy, genetic disease, autoimmune disease, myopathy (ICD-10 classes M60-M63), osteopathy (ICD-10 classes M80 to M90), osteoporosis, chondropathy (ICD-10 classes M91 to M94), vasculopathy, viral infection, fungal infection, bacterial infection, parasite, side effect of a drug, surgical procedure, medical examination, calcification, trauma unless induced by physical activity, malformation, or combinations thereof.

"Neurodegenerative disease" is a progressive pathology that affects the brain or, more globally, the nervous system, leading to the death of nerve cells. "Neuropathy" refers to all diseases substantially of the peripheral nervous system, i.e., motor and sensory nerves and limbs, nerves of the autonomic nervous system that control the organs, and more rarely of the central nervous system. Neuropathies can be caused by, but are not limited to, alcohol abuse, medication, diabetes, viral infection, injury to a nerve, or an unknown cause.

"Genetic disease" is a disease caused by one or more abnormalities on one or more chromosomes that result in the malfunction of certain cells in the body. A genetic disease may be due to a deletion or mutation on a gene leading to the formation of a non-active or malformed protein.

An autoimmune disease is a disease in which the immune system is overactive and attacks normal human cells.

Myopathy is a degenerative muscle disease characterized by a decrease in the strength of the affected muscles and a variable degree of atrophy. They are most often hereditary diseases. "Chondropathy" is a disease affecting the cartilage and may be due to excessive or poorly distributed pressure on the cartilage. It may manifest itself as a softening of the cartilage. "Osteoporosis" is a rarefaction of bone tissue and can be caused by menopause, age, or be idiopathic. "Vasculopathy" is a pathology affecting the arterial or venous vessels.

"Trauma" is defined as a fracture, sprain, dislocation, subluxation, muscle tear, ligament, or tendon injury, or combinations thereof.

There are different scales for measuring pain, and in particular joint pain. Such measurement scales are listed, for example, in the document provided by the Haute Autorité de Santé (https://www.has-sante.fr/upload/docs/application/pdf/2019-02/liste_echelles_douleur_2019.pdf). Among these scales, reference is made in particular to the visual analogue scale of pain, the numerical scale and the simple verbal scale. Some scales have been developed for particular categories of the population. For example, the Doloplus and Algoplus scales are specifically developed for the elderly.

Various scales have been proposed for joint pain, including the Western Ontario and McMaster Universities Arthritis Index (WOMAC). These scales can be used to assess all types of joint pain, including knee joint pain, regardless of the etiology.

Specifically, the WOMAC score is calculated based on the answers to the questions below:
1) Pain (5 items scored from 0-100): How bad is the pain?
  a) Item 1. When you walk on a flat surface?
  b) Item 2. When you go up or down the stairs?
  c) Item 3. At night when you are in bed?
  d) Item 4. When you stand up from a chair or sit down?
  e) Item 5. When you stand upright?
2) Joint stiffness (2 items scored from 0-100): How much stiffness do you have in your joint?
  a) Item 1. When you get up in the morning?
  b) Item 2. When you move after sitting, lying down, or resting during the day?
3) Joint Function (17 items scored from 0-100): How much difficulty do you have with:
  a) Item 1. Going down the stairs?
  b) Item 2. Going up the stairs?
  c) Item 3. Getting up from a sitting position?
  d) Item 4. Standing upright?
  e) Item 5. Bending forward?
  f) Item 6. Walking on flat ground?
  g) Item 7. Getting in and out of a car?
  h) Item 8. Going shopping?
  i) Item 9. Putting on tights or socks?
  j) Item 10. Getting out of bed?
  k) Item 11. Taking off your tights or your socks?
  l) Item 12. Lying down in bed?
  m) Item 13. Getting in or out of a bathtub?
  n) Item 14. Sitting down?
  o) Item 15. Sitting down and getting up from the toilet?
  p) Item 16. "Thoroughly" cleaning the house?
  q) Item 17. During daily housekeeping?

The total score is the average of the 24 items. The same is true for the score of each area. The total score measuring joint pain reflects the component of these three sub-areas: pain, stiffness, and function.

As for the Lequesne score, it varies from 0 to 22: the higher the score, the more extreme or even unbearable the handicap. From 8 to 10, the handicap is qualified as significant and for an index greater than or equal to 10, the handicap is qualified as very significant.

In particular, NMN, one of the derivatives thereof or the pharmaceutically acceptable salts thereof, or compositions comprising same can be used to improve joint pain parameters, joint stiffness, and/or improve joint function as assessed by the WOMAC index.

"Joint function" refers to the use of the joint. For example, the assessment of knee joint function includes questions about walking without pain, climbing stairs, sitting down, getting in and out of a vehicle, bending over, getting up from a chair, standing without difficulty, shopping, dressing, lying down without pain, and cleaning.

Use

According to the present invention, NMN, the pharmaceutically acceptable derivatives thereof, or the pharmaceutically acceptable salts thereof, as well as compositions comprising same are used to prevent and/or treat joint pain resulting from physical activity.

The physical activity that can cause joint pain depends on the physical condition of the person and the nature of the physical activity.

The physical activity can be either recreational, occupational, or athletic. Examples of recreational physical activities include, but are not limited to, walking, shopping, DIY, assembling furniture, gardening, fishing, cooking. The physical activity that can lead to joint pain can be, for example, a job requiring physical manipulation such as a physiotherapist, osteopath, nurse, care assistant, stretcher-bearer, fireman, first-aid worker, surface technician, storekeeper, salesman, security guard, and others.

The intensity of different forms of physical activity varies from person to person. To be beneficial from a cardiorespiratory endurance perspective, all activity should be performed in increments of at least 10 minutes. In its Global Physical Activity Questionnaire, the WHO provides examples of intense and moderate physical activity, both at work and at play. For example, high-intensity physical activity requires a significant increase in breathing or heart rate, such as heavy lifting, working on a construction site, doing masonry work, running, or playing soccer for at least 10 minutes at a time. Moderate-intensity physical activity can be brisk walking or light lifting, swimming, cycling, or playing volleyball for at least 10 minutes at a time. The WHO also considers how you get from one place to another, such as walking or cycling, as part of physical activity. A low intensity physical activity can be, for example, slow walking or doing the dishes, a moderate intensity physical activity can be brisk walking or water aerobics, and a high intensity physical activity can be jogging or tennis.

There are 4 levels of activity intensity, the physical intensity being dependent on the feeling of each individual:

Low-intensity activities—such as driving a car, tidying, cooking—do not cause shortness of breath or sweating. The effort felt is estimated at 3 or 4 on a scale of 0 to 10.

Moderate-intensity activities—such as brisk walking, running (less than 5 miles per hour), biking (approximately 10 miles per hour), or climbing stairs—cause moderate shortness of breath and slight sweating. The effort is estimated at 5 or 6 on a scale of 0 to 10. Holding a conversation is possible.

High-intensity activities—such as walking fast or uphill, running, cycling (approximately 20 km/h) or moving heavy loads—cause marked shortness of breath and profuse sweating. The effort is estimated at 7 or 8 on a scale of 0 to 10. Holding a conversation is difficult.

Very high intensity activities—such as running (9 to 18 km/h), cycling (more than 25 km/h), jumping rope—cause very severe shortness of breath and profuse sweating. The effort is estimated to be more than 8 on a scale of 0 to 10. Holding a conversation is impossible.

Preferably, the joint pain results from playing sports.

Examples of sports that cause joint pain include, but are not limited to, hiking, Nordic walking, race walking, horseback riding, athletics, dance, gymnastics, racquet sports, combat sports, team sports, water sports, and extreme sports. Examples of racket sports are tennis, badminton, squash, ping-pong, and court tennis. Examples of combat sports include martial arts, French boxing, English boxing, Thai boxing, fencing, wrestling, capoeira, wrestling, and savate. Examples of team sports include, but are not limited to, soccer, handball, volleyball, basketball, rugby, polo, and water polo. Examples of water sports include kayaking, sailing, windsurfing, diving, and canoeing. Examples of extreme sports include, but are not limited to, skydiving, paragliding, kitesurfing, surfing, wakeboarding, canyoning, mountaineering, and rock climbing.

NMN, one of the derivatives thereof, or the salts thereof, as well as the compositions comprising same according to the invention, can be used to relieve joint pain, in particular gonalgia, related to playing sports, without having to resort to using conventional therapies.

In particular, NMN, a pharmaceutically acceptable derivative thereof, or a pharmaceutically acceptable salt thereof, as well as compositions comprising same, can be used in treating and/or preventing joint pain, preferably gonalgia, induced by physical activity in mammals, preferably humans.

Pain can affect any joint in the human body, including the neck, shoulder, scapula, elbow, wrist, hand joints, hip, sacroiliac joint, knee, ankle, foot joints, or combinations thereof.

Preferably, the joint pain concerns the knee (gonalgia). The use according to the present invention is particularly effective in relieving knee pain.

Method of Administration and Dosage Form

NMN, a pharmaceutically acceptable salt thereof, a pharmaceutically acceptable derivative thereof, and compositions comprising same are administered topically. "Topically" means the form of administration of a composition or substance to an external point or surface of the body, such as the skin or mucosa.

The dosage forms suitable for the implementation of the invention are a gel, a solution, a water-in-oil emulsion, an oil-in-water emulsion, a cream, an ointment, or a liniment.

"Solution" means a liquid dosage form used for administering at least one active ingredient obtained by dissolving the different ingredients in a liquid phase and forming a single homogeneous phase.

"Emulsion" means a heterogeneous mixture of two immiscible liquids, one of which is dispersed in the form of small droplets in the other. An emulsion is a mixture of two liquids that do not mix spontaneously (immiscible), such as water and oil. An emulsion can be obtained using specific operations (agitation, mixing, addition of some active principles). An emulsion has a macroscopically homogeneous aspect, but microscopically heterogeneous. One of the substances is dispersed in the second substance in the form of droplets. The mixture can remain stable using a third ingredient called an emulsifier (progression speed or kinetics of the mixture almost zero). A "water-in-oil emulsion" is composed of an aqueous phase dispersed in an oily phase. An "oil-in-water emulsion" is composed of an oily phase dispersed in an aqueous phase.

"Cream" means a semi-solid preparation intended for topical administration.

"Ointment" means a semi-solid preparation intended to be applied to the skin.

"Liniment" is a liquid pharmaceutical form, classically comprising fatty substances such as oils, intended to be used in friction.

"Gel" means a solid, possibly ductile, material consisting of a three-dimensional network of macromolecules surrounded by liquid. A composition in the form of a gel penetrates well and quickly into the skin and also makes it possible to provide an anesthetic sensation of freshness.

In a preferred embodiment, the gel may be a hydrophobic gel or a hydrophilic gel. Preferably, the gel is a hydrophilic gel.

In a particularly preferred embodiment, the composition according to the invention is in the form of a water-in-oil emulsion or an oil-in-water emulsion, more preferably in the form of an oil-in-water emulsion (noted as oil/water or O/W).

NMN is very hydrophilic and therefore solubilizes best in aqueous phases.

The composition according to the invention may comprise NMN, one of the salts thereof, or one of the pharmaceutically acceptable derivatives thereof, in an amount of between 0.05% and 15% by weight, preferably between 1 and 10% by weight, more preferably between 3 and 5% by weight relative to the total weight of the composition.

NMN, a pharmaceutically acceptable derivative thereof, or a pharmaceutically acceptable salt thereof, may be administered between 1 and 10 times per day, preferably between 1 and 5 times per day, more preferably between 1 and 3 times per day.

In a preferred embodiment, NMN, a pharmaceutically acceptable derivative thereof, or a pharmaceutically acceptable salt thereof, or the composition comprising same may be administered twice daily.

Therapeutic Combinations

NMN, a pharmaceutically acceptable derivative thereof, a pharmaceutically acceptable salt thereof, and compositions comprising same may also be used in combination with at least one other therapeutic agent, in particular therapeutic agents conventionally used for relieving joint pain resulting from physical activity.

Therapeutic agents that may be combined with the invention include an analgesic, a non-steroidal anti-inflammatory drug, cortisone, a cortisone derivative, and combinations thereof.

The analgesic can be selected from paracetamol, nefopam, ketanin, tetrahydrocannabinol, cannabinoids, aspirin, methyl salicylate, diflunisal, salicylamide, codeine, alfentanil, carfentanil, dihydrocodeine, codeinone, tramadol, morphine, buprenorphine fentanyl, acetyl fentanyl, remifentanil, sufentanil, heroin, hydromorphone, nalbuphine, oxycodone, hydroxycodone, oxymorphone, laudanum, methadone, pethidine, dextropropoxyphene, endorphin, tapentadol, thebaine, vicodin, and combinations thereof.

The non-steroidal anti-inflammatory drug (NSAID) may be selected from ibuprofen, ketoprofen, naproxen, ketorolac, alminoprofen, aceclofenac, mefenamic acid, niflumic acid, tiaprofenic acid, celecoxib, rofecoxib, valdecoxib, parecoxib, dexketoprofen, diclofenac, etodolac, etoricoxib, fenoprofen, flurbiprofen, indomethacin, meloxicam, nabumetone, piroxicam, sulindac, tenoxicam, nimesulide, and combinations thereof.

The cortisone derivative can be selected from betamethasone, ciprofloxacin, cortivazol, dexamethasone, fludrocortisone, methylprednisolone, prednisolone, and triamcinolone, and combinations thereof.

The at least one additional therapeutic agent may be administered either topically, by injection, or orally. More specifically, the at least one additional therapeutic agent may be administered in the manner in which it is conventionally administered.

The at least one other therapeutic agent may also be administered concomitantly or at different times from the NMN, a pharmaceutically acceptable salt or derivative thereof, or the composition according to the invention.

Compositions

The compositions according to the invention may comprise nicotinamide mononucleotide, a pharmaceutically acceptable derivative thereof, or a pharmaceutically acceptable salt thereof, and at least one pharmaceutically acceptable excipient for preventing and/or treating joint pain induced by physical activity, administered topically.

Such compositions are particularly useful for relieving joint pain induced by physical activity, in particular resulting from playing sports as described in the description.

In the context of the present invention, an "excipient" refers to any substance other than NMN in the composition and having no therapeutic effect. The excipient does not chemically interact with the NMN or any additional therapeutic agent.

The excipient can be chosen from a bulking agent, a lubricant, a perfume, a colorant, an emulsifier, a compression agent, a diluent, a preservative, a gelling agent, a plasticizer, a surfactant, or combinations thereof. A person skilled in the art would know which excipient to choose according to the dosage form he has chosen.

The composition according to the invention may be a pharmaceutical composition.

In an interesting variant, the composition according to the invention may further comprise at least one additional therapeutic agent as defined above for use in preventing and/or treating joint pain induced by physical activity, in particular sports.

Process for the Preparation of Compounds of Formula (I) and (Ia)

The compounds of formula (I) or formula (Ia) can be prepared by any method well known to a person skilled in the art.

Process for the Preparation of Compounds of Formula (I)

The compounds of formula (I) can be prepared according to the process described in international application WO 2017/024255A1 as well as the method described below.

In particular, the compounds of formula (I) disclosed herein can be prepared as described below from the substrates A-E. It will be understood by a person skilled in the art that these reaction schemes are by no means limiting and that variations may be made without departing from the spirit and scope of the present invention.

According to one embodiment, the invention relates to a method for preparing the compounds of formula (I) as described above.

The method involves, in a first step, the mono-phosphorylation of a compound of formula (A), in the presence of phosphoryl chloride and a trialkyl phosphate, to yield the phosphorodichloridate of formula (B),

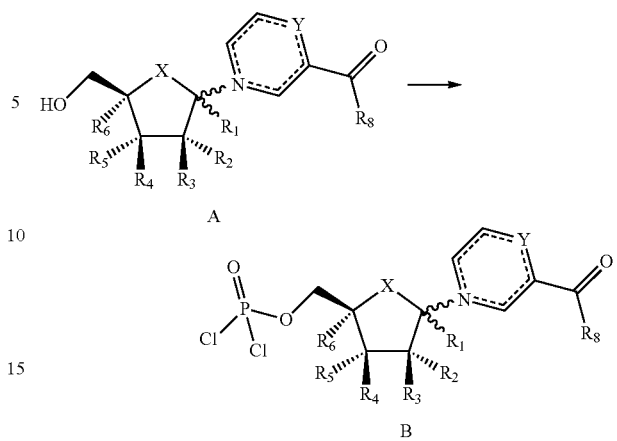

wherein X, $R_1$, $R_2$, $R_3$, $R_4$, $R_5$, $R_6$, $R_8$, Y, ~~~~, and ~~~~ are as defined above for the compounds of formula (I).

In a second step, the phosphorodichloridate of formula (B) is hydrolyzed to yield the phosphate of formula (C),

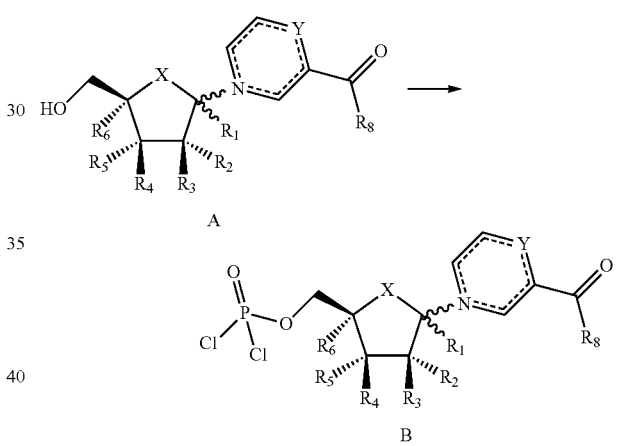

wherein X, $R_1$, $R_2$, $R_3$, $R_4$, $R_5$, $R_6$, $R_8$, Y, ~~~~, and ~~~~ are as defined above for the compounds of formula (I).

According to one embodiment, the compound of formula (A) is synthesized using various methods known to a person skilled in the art.

According to one embodiment, the compound of formula (A) is synthesized by reacting pentose of formula (D) with a nitrogen derivative of formula (E), wherein R, $R_2$, $R_3$, $R_4$, $R_5$, $R_6$, $R_7$, Y are as described above for compounds of formula I, yielding the compound of formula (A-1) which is then selectively deprotected to yield the compound of formula (A),

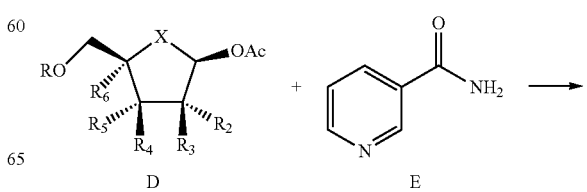

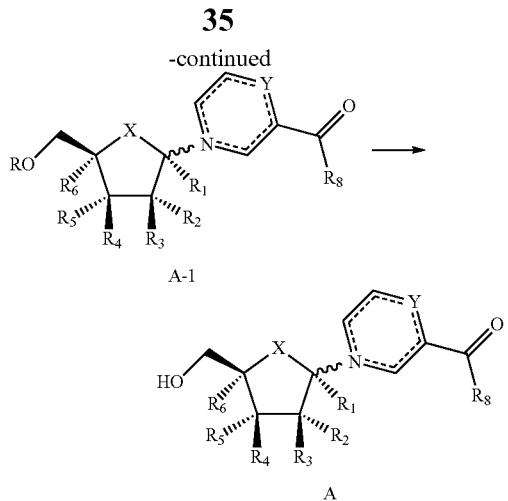

wherein X, $R_1$, $R_2$, $R_3$, $R_4$, $R_5$, $R_6$, $R_8$, Y, ═══, and ∿∿∿ are as defined above for the compounds of formula (I).

According to one embodiment, R is a suitable protecting group known to a person skilled in the art. In one embodiment, the protecting group is selected from triarylmethyl and/or silyl. Non-limiting examples of triarylmethyl include trityl, monomethoxytrityl, 4,4'-dimethoxytrityl, and 4,4',4"-trimethoxytrityl. Non-limiting examples of silyl groups include trimethylsilyl, tert-butyldimethylsilyl, triisopropylsilyl, tert-butyldiphenylsilyl, tri-iso-propylsilyloxymethyl, and [2-(trimethylsilyl)ethoxy]methyl.

According to one embodiment, any hydroxyl group attached to the pentose is protected by a suitable protecting group known to a person skilled in the art.

The selection and exchange of protecting groups is within the skills of a person skilled in the art. The protecting groups can also be removed by methods well known to a person skilled in the art, for example, with an acid (e.g., mineral or organic acid), a base, or a fluoride source.

In a preferred embodiment, the nitrogen derivative of formula (E) is coupled to the pentose of formula (D) by a reaction in the presence of a Lewis acid, yielding the compound of formula (A-1). Non-limiting examples of Lewis acids include TMSOTf, $BF_3.OEt_2$, $TiCl_4$, and $FeCl_3$.

In one embodiment, the method of the present invention further comprises a step of reducing the compound of formula (A) by various methods well known to a person skilled in the art, yielding the compound of formula (A'), wherein $CH_2$ and $R_1$, $R_2$, $R_3$, $R_4$, $R_5$, $R_6$, $R_8$, Y, ═══, and ∿∿∿ are as defined above for compounds of formula (I).

In a particular embodiment, the present invention relates to a method for preparing the compounds of formula I-A, I-C, I-E, I-G.

In a first step, nicotinamide of formula E is coupled to ribose tetraacetate of formula D by a coupling reaction in the presence of a Lewis acid, yielding the compound of formula A-1:

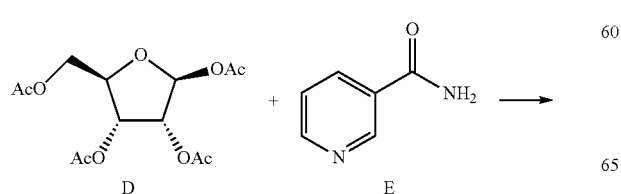

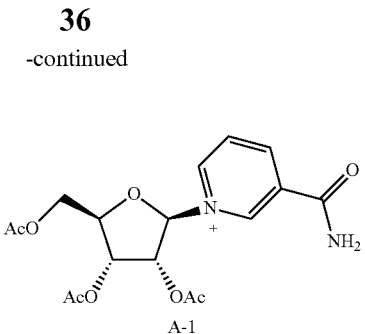

In a second step, an ammonia treatment of the compound of formula A-1 is performed, yielding the compound of formula I-A:

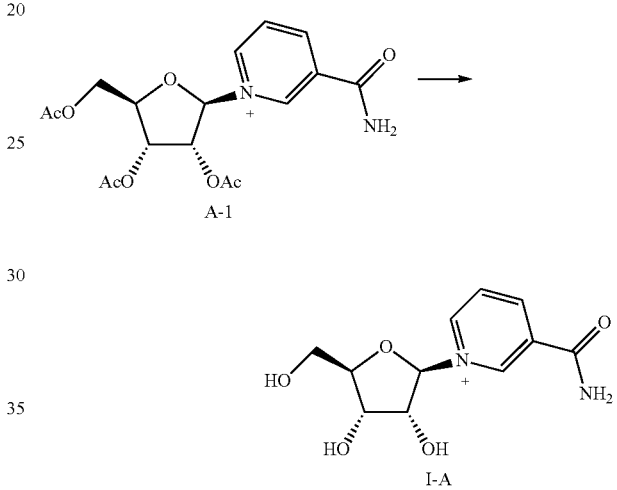

In a third step, the mono-phosphorylation of the compound of formula I-A, in the presence of phosphoryl chloride and a trialkyl phosphate, yields the phosphorodichloridate of formula I-A':

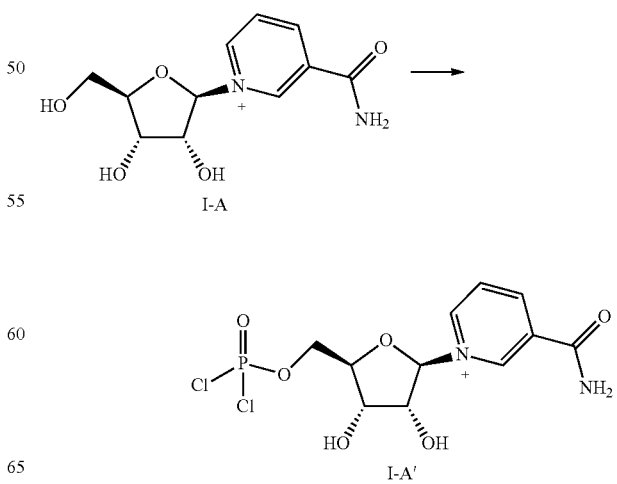

In a fourth step, the phosphorodichloridate of formula B is hydrolyzed to yield the compound of formula I-C:

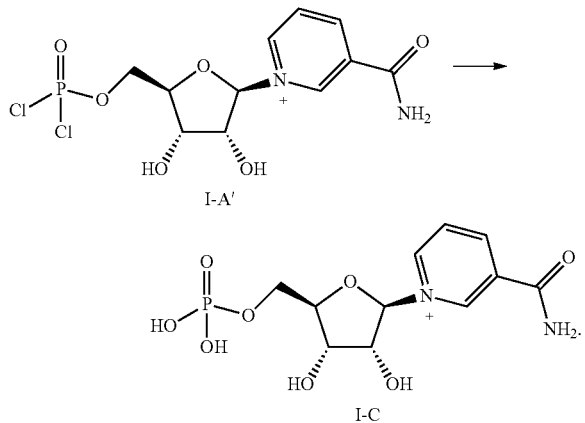

In one embodiment, a step of reducing the compound of formula I-A is performed, yielding the compound of formula I-E.

The compound of formula I-E is then mono-phosphorylated as described in step four and hydrolyzed to yield the compound of formula I-G.

According to one embodiment, the compounds of formula (I) are selected from compounds I-A to I-J in the table below:

TABLE 1

| Compounds (anomers) | Structure |
|---|---|
| I-A (beta) | |
| I-B (alpha) | |
| I-C (beta) | |
| I-D (alpha) | 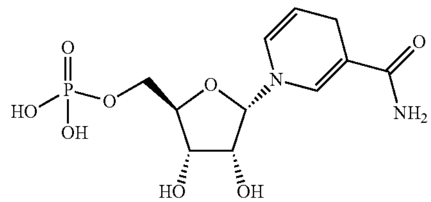 [SMILES: NC(=O)C1=CN([C@H]2O[C@H](COP(=O)(O)O)[C@@H](O)[C@H]2O)C=CC1] |
| I-E (beta) | 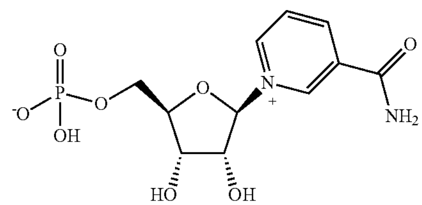 |
| I-F (alpha) | 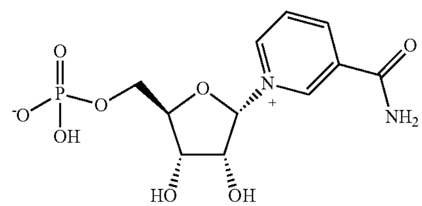 |
| I-G (beta) | 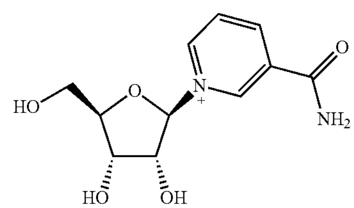 |
| I-H (alpha) | 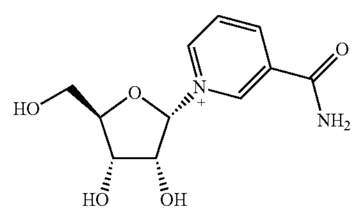 |
| I-I (beta) | 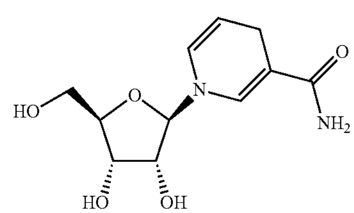 [SMILES: NC(=O)C1=CN([C@@H]2O[C@H](CO)[C@@H](O)[C@H]2O)C=CC1] |
| I-J (alpha) | 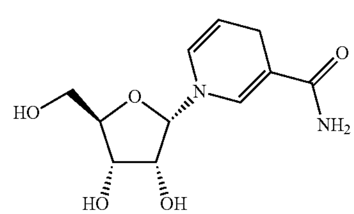 [SMILES: NC(=O)C1=CN([C@H]2O[C@H](CO)[C@@H](O)[C@H]2O)C=CC1] |

Preferably, the compound of formula (I) is selected from compound I-A, compound I-B, compound I-C, compound I-D, compound I-E, compound I-F, compound I-G, compound I-H, compound I-I, compound I-J, preferably compound I-C, compound I-D, or compound I-F, and combinations thereof. More preferably, the compound of formula (I) is selected from compound I-B, compound I-C, compound I-D, compound I-F, and combinations thereof.

Process for the Preparation of the Derivatives of Formula (Ia)

In particular, the compounds of formula Ia disclosed herein can be prepared as described below from substrates X-XIII. It will be understood by an ordinary person skilled in the art that these schemes are in no way limiting and that variations in detail may be made without departing from the spirit and scope of the present invention.

According to one embodiment, the invention relates to a method for preparing the compound of formula I described above.

The method consists first of mono-phosphorylating a compound of formula X, in the presence of phosphoryl chloride in a trialkyl phosphate, to obtain the phosphorodichloridate compound XI,

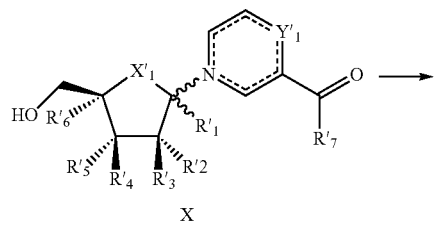

X

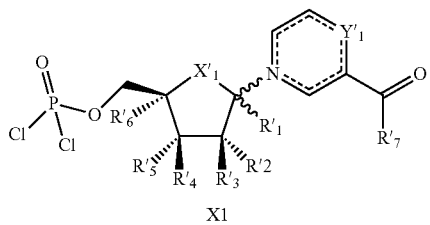

XI wherein $X'_1$, $R'_1$, $R'_2$, $R'_3$, $R'_4$, $R'_5$, $R'_6$, $R'_7$, $Y'_1$, ━━━, and ∿∿∿ are as defined above.

In a second step, hydrolysis of the phosphorodichloridate XI obtained in the first step yields the phosphate compound of formula XII,

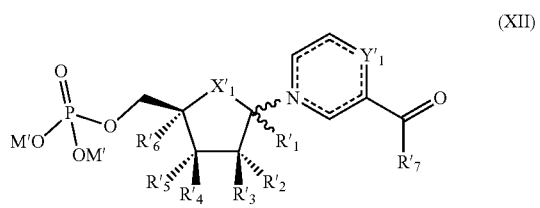

(XII)

wherein $X'_1$, $R'_1$, $R'_2$, $R'_3$, $R'_4$, $R'_5$, $R'_6$, $R'_7$, $Y'_1$, ━━━, and ∿∿∿ are as defined above.

The phosphate compound of formula XII obtained in the second step is then reacted with a phosphorodichloridate compound of formula XIII obtained as described in the first step,

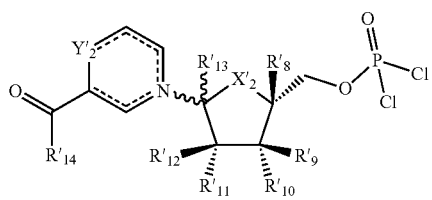

wherein $X'_2$, $R'_8$, $R'_9$, $R'_{10}$, $R'_{11}$, $R'_{12}$, $R'_{13}$, $R'_{14}$, $Y'_2$, ━━━ and ∿∿∿ are as described herein for formula Ia, to yield the compound of formula Ia as described herein.

According to one embodiment, the process further comprises a step of reducing the compound of formula Ia, using various methods known to those skilled in the art, to yield the compound of formula Ia, wherein $Y'_1$ and $Y'_2$ are identical and each represents $CH_2$ and wherein $X'_1$, $X'_2$, $R'_1$, $R'_2$, $R'_3$, $R'_4$, $R'_5$, $R'_6$, $R'_7$, $R'_8$, $R'_9$, $R'_{10}$, $R'_{11}$, $R'_{12}$, $R'_{13}$, $R'_{14}$, $Y'_1$, $Y'_2$, and ━━━ ∿∿∿ are as described herein for formula Ia.

In one variant, R is a suitable protecting group known to those skilled in the art. Examples of suitable protecting groups include triarylmethyl and/or silyl. Non-limiting examples of triarylmethyl include trityl, monomethoxytrityl, 4,4'-dimethoxytrityl and 4,4',4"-trimethoxytrityl. Non-limiting examples of silyl groups include trimethylsilyl, tert-butyldimethylsilyl, triisopropylsilyl, tert-butyldiphenylsilyl, tri-iso-propylsilyloxymethyl and [2-(trimethylsilyl)ethoxy]methyl.

According to one embodiment, any hydroxyl group attached to the pentose ring is protected by an appropriate protection group known to those skilled in the art.

The selection and exchange of protection groups is within the skills of those skilled in the art. Any protection group can also be removed by methods known in the art, for example, with an acid (e.g., mineral or organic acid), base, or fluoride source.

According to a preferred embodiment, the nitrogen derivatives of formula XV are added to pentose XIV by a coupling reaction in the presence of a Lewis acid to yield the compound of formula X-1. Non-limiting examples of suitable Lewis acids include TMSOTf, $BF_3 \cdot OEt_2$, $TiCl_4$ and $FeCl_3$.

According to a specific embodiment, the invention relates to a method for preparing the compound of formula VIII,

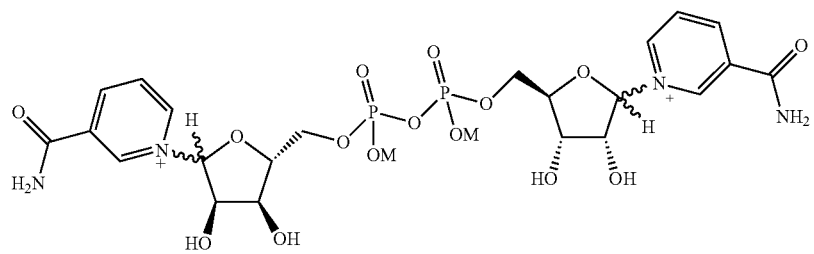

or the pharmaceutically acceptable salts and/or solvates thereof.

In a first step, nicotinamide of formula XV is added to ribose tetraacetate XIV by a coupling reaction in the presence of a Lewis acid to yield the compound of formula X-1:

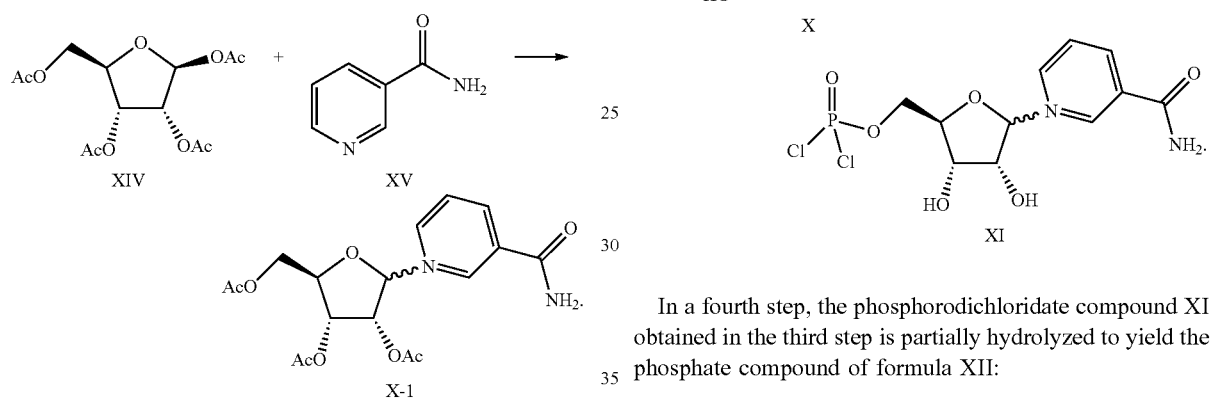

In a second step, an ammonia treatment of the compound of formula X-1 yields the compound of formula X:

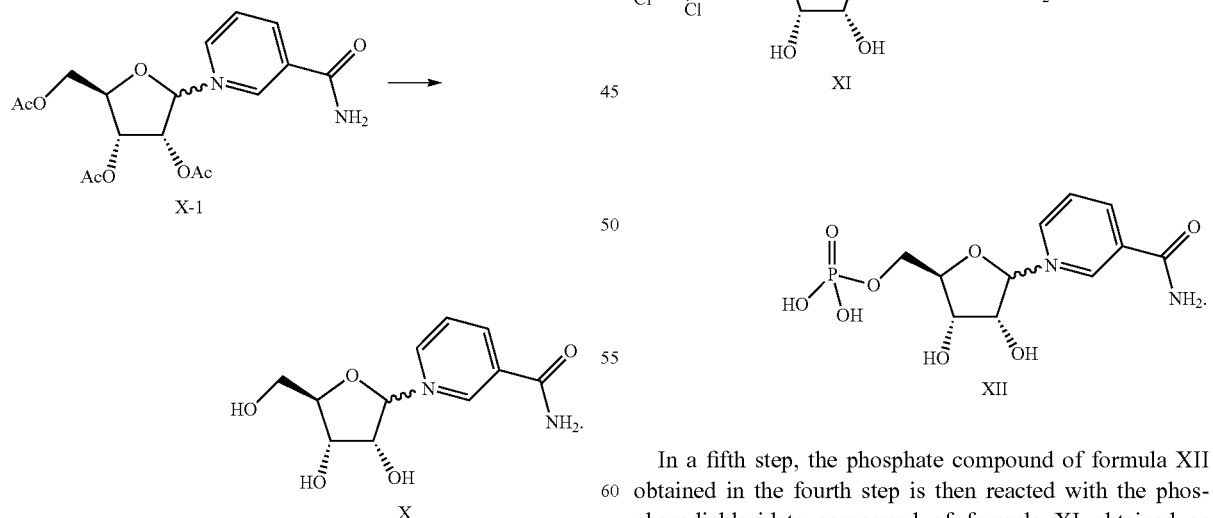

In a third step, the mono-phosphorylation of a compound of formula X, in the presence of phosphoryl chloride in a trialkyl phosphate, yields the phosphorodichloridate compound XI:

In a fourth step, the phosphorodichloridate compound XI obtained in the third step is partially hydrolyzed to yield the phosphate compound of formula XII:

In a fifth step, the phosphate compound of formula XII obtained in the fourth step is then reacted with the phosphorodichloridate compound of formula XI obtained as described in the third step to obtain the compound of formula VIII.

According to another specific embodiment, the invention relates to a method for preparing the compound of formula IX,

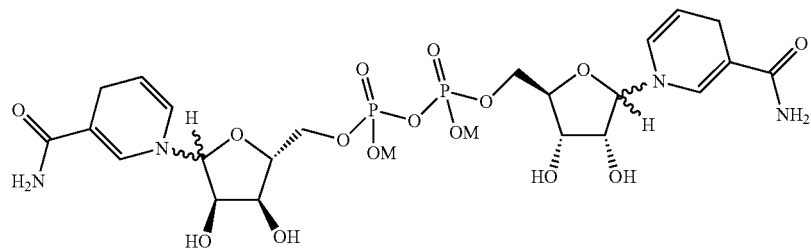

or the pharmaceutically acceptable salts and/or solvates thereof.

According to one variant, the compound of formula IX is obtained from the compound of formula VIII, previously synthesized as described above.

In this embodiment, the compound of formula IX is obtained by reducing the compound of formula VIII, using a suitable reducing agent known to those skilled in the art, to yield the compound of formula IX.

According to one embodiment, the preferred compounds of the invention are compounds Ia-A to Ia-I of Table 2:

TABLE 2

| Compounds (anomers) | Structure |
|---|---|
| Ia-A (beta, beta) | 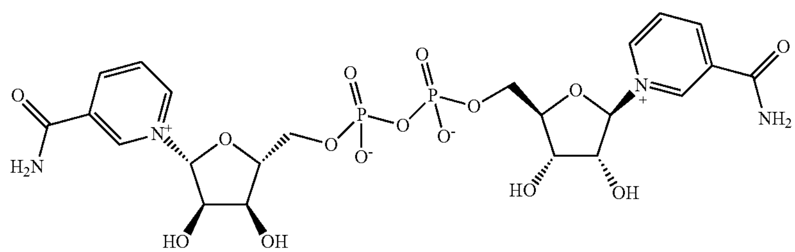 |
| Ia-B (beta, alpha) | 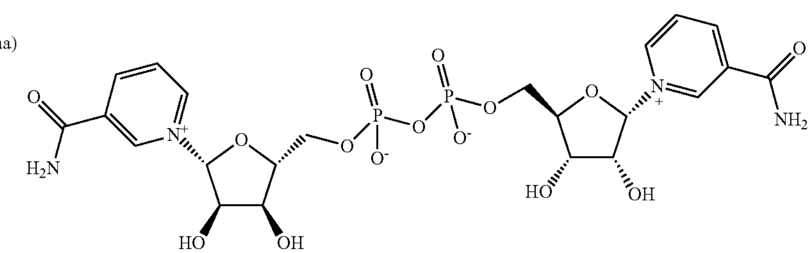 |
| Ia-C (alpha, alpha) | 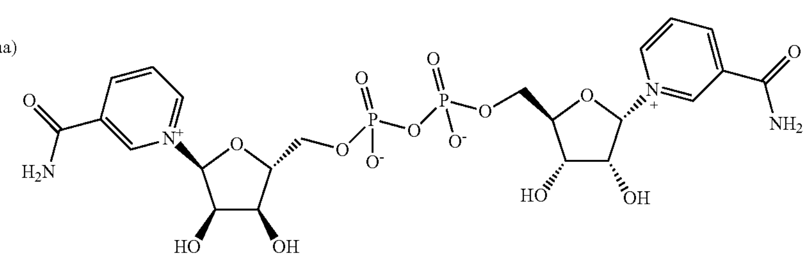 |
| Ia-D (beta, beta) | 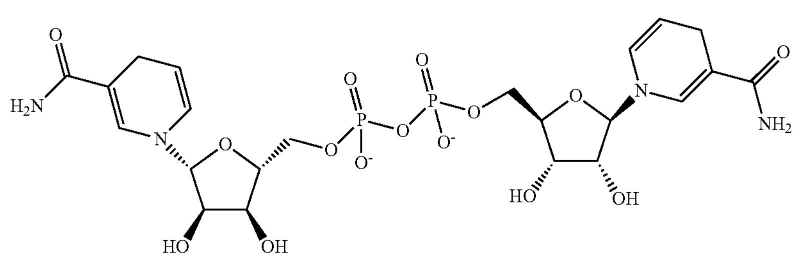 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |

TABLE 2-continued

| Compounds (anomers) | Structure |
|---|---|
| Ia-E (beta, alpha) | 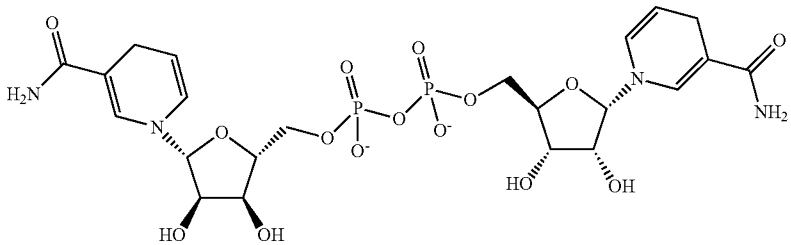 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| Ia-F (alpha, alpha) | 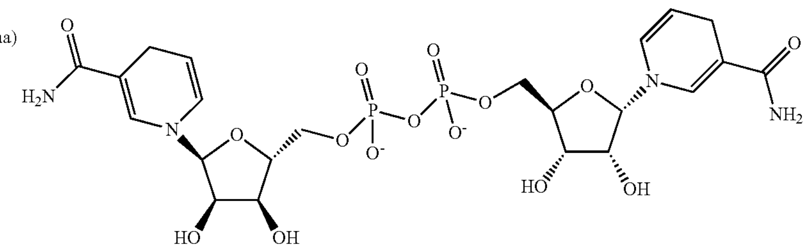 |
| Ia-G (beta, beta) | 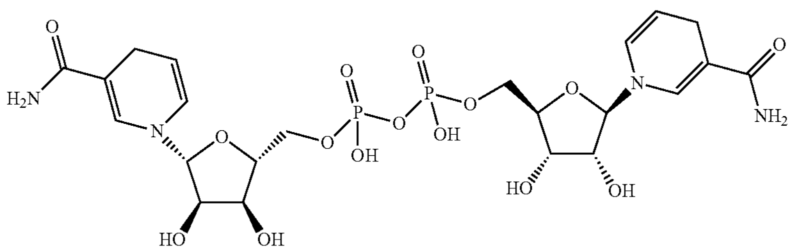 [SMILES: NC(=O)C1=CN([C@@H]2O[C@H](COP(=O)(O)OP(=O)(O)OC[C@H]3O[C@@H](N4C=CCC(C(N)=O)=C4)[C@H](O)[C@@H]3O)[C@@H](O)[C@H]2O)C=CC1] |
| Ia-H (beta, alpha) | 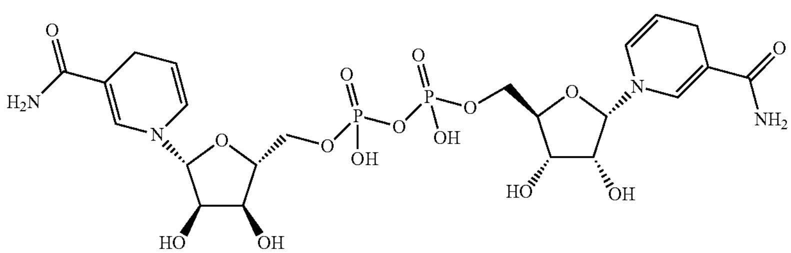 [SMILES: NC(=O)C1=CN([C@@H]2O[C@H](COP(=O)(O)OP(=O)(O)OC[C@H]3O[C@H](N4C=CCC(C(N)=O)=C4)[C@H](O)[C@@H]3O)[C@@H](O)[C@H]2O)C=CC1] |
| Ia-I (alpha, alpha) | 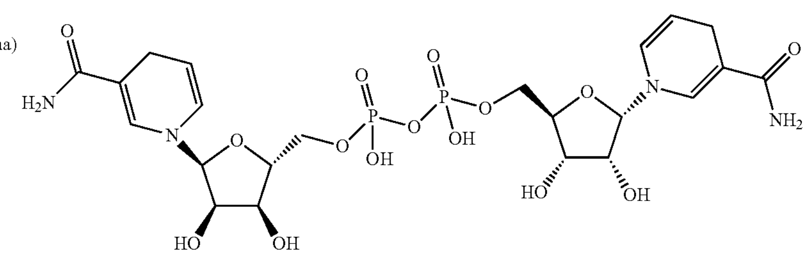 |

Preferably, the compound of formula (Ia) is selected from the compound of formula Ia-B, the compound of formula Ia-C, the compound of formula Ia-E, the compound of formula Ia-F, the compound of formula Ia-H, the compound of formula Ia-I and the compound of formula Ia-G as well as combinations thereof.

FIGURES

FIG. 1 is a graph showing the progression of pain intensity.

EXAMPLE

In the remainder of the present description, the examples are provided for illustrative purposes of the present invention and are in no way intended to limit the scope thereof.

A satisfaction study was conducted in a group of 12 volunteers, aged 37±9 years, composed of eight men and four women. The main objective of this study was to evaluate the satisfaction of the persons with regard to the progression of their acute knee pain during the morning and/or evening application of a gel containing 5% by weight of NMN.

The average BMI of the participants was 26.0±3.9. More precisely, six participants were of normal weight, four participants were overweight, and two participants were obese. None of these patients had chronic pathology such as osteoarthritis, inflammatory pathology altering their cartilage, muscles, tendons, ligaments, or bones, or requiring surgery.

The average length of time during which knee pain had existed at the time of the study was 6.3±1.9 days, with a median of 7 days, whereas the subjects' current pain dated back to 6±2 days before inclusion. Most of the pain occurred after physical activity (91.7%). One person had spontaneous pain. The 11 other volunteers had pain after playing sports or physical activity.

A composition in the form of an oil-in-water emulsion comprising 5% NMN was formulated as follows, the ingredients being designated by their INCI names: aqua, paraffinum liquidum, cetyl alcohol, glyceryl stearate, benzyl PCA, ceteareth-20, ceteareth-12, cetyl palmitate, cocoglycerides, cetearyl alcohol, sodium hydroxide, NMN.

The mass percentages are calculated by taking the mass of the ingredient in relation to the total mass of the composition and multiplying by 100.

The study was conducted over 10 days. At inclusion (D0), the selected subjects provided their demographic characteristics (age, weight, height), indicated the duration and intensity of pain on a visual analog scale, and completed the WOMAC and Lequesne questionnaires. Although none of the patients had osteoarthritis or arthritis, the Lequesne and WOMAC questionnaires were used to assess the effect of NMN on knee joint pain in different ways.

The WOMAC score is a validated scale for evaluating gonalgia and is recognized by the Haute Autorité de Santé and the Société Française de Rhumatologie. The WOMAC score is composed of 24 questions, the answers to which are visual analog scales ranging from 0 (minimum) to 100 (maximum), in 3 evaluation areas: pain with 5 questions, stiffness with 2 questions and daily function with 17 questions. The total score is calculated by averaging the 24 responses and is evaluated from 0 (no impact) to 100 (maximum impact). The higher the WOMAC score, the greater the functional impact.

The WOMAC "pain" dimension was the most significant at inclusion and amounted to 57.1±7.4, the "stiffness" dimension to 54.3±19.1, and the "function" dimension to 41.5±17.9. The total WOMAC score was 45.8±14.3 at inclusion.

The Lequesne algofunctional index is used for the clinical follow-up of gonalgia and as an evaluation tool for the indication of a prosthesis. The Lequesne score varies from 0 to 22, the higher the score, the more extreme or even unbearable the handicap. From 8 to 10, the handicap is qualified as significant and for an index greater than or equal to 10, a prosthesis can be indicated.

The Lequesne score at inclusion was 8.0±2.4, and 2 of the subjects had a score greater than or equal to 10 (16.7%).

During the following 9 days, the persons fill in the visual analog scale of pain every evening and note the occurrence of any discomfort or the use of painkillers.

On the 10th day, the volunteers fill out the WOMAC questionnaire, the Lequesne questionnaire, the visual analog scale (VAS) of pain, the perceived improvement of the pain measured by the PGI-I (Patient Global Improvement Impression) index, satisfaction with the progression of the gonalgia on a Lickert scale, as well as the ease of application and penetration of the gel, appreciation of the texture and smell of the gel, repeated use thereof if the same pain reappeared, and recommendation to others who would have the same type of pain. The PGI-I is an index to assess the response to treatment. The Likert scale is a psychometric tool for measuring attitudes in individuals, consisting of one or more statements for which the respondent expresses agreement or disagreement.

Compliance with treatment was 95.8±8.2% on average during the study.

Pain, as measured by the VAS scale, decreased steadily over the 10 days of application of the product, from 66.8±5.0 at inclusion to 18.9±18.8, i.e., a significant reduction of 47.9±20.1 points (p<0.0001). The mean time to achieve a 50% reduction in pain compared to inclusion was 5±2 days. The results expressed as mean and standard deviation, day by day and for all volunteers, are summarized in Table 3 below:

TABLE 3

| Pain | N | Average | Standard deviation | Median | Minimum | Maximum |
|---|---|---|---|---|---|---|
| Inclusion D 0 | 12 | 66.8 | 5.0 | 65.5 | 61.0 | 80.0 |
| D 1 | 12 | 53.8 | 12.8 | 57.5 | 22.0 | 64.0 |
| D 2 | 12 | 52.5 | 12.0 | 50.0 | 25.0 | 71.0 |
| D 3 | 12 | 43.8 | 9.8 | 43.5 | 29.0 | 60.0 |
| D 4 | 12 | 40.1 | 14.1 | 39.0 | 11.0 | 61.0 |
| D 5 | 12 | 35.6 | 13.3 | 36.5 | 9.0 | 60.0 |
| D 6 | 12 | 36.0 | 15.7 | 34.5 | 12.0 | 72.0 |
| D 7 | 12 | 29.8 | 15.7 | 24.5 | 14.0 | 69.0 |
| D 8 | 12 | 23.5 | 14.5 | 19.0 | 0.0 | 55.0 |
| D 9 | 12 | 22.2 | 17.7 | 19.5 | 0.0 | 51.0 |
| End of study D 10 | 12 | 18.9 | 18.8 | 18.0 | 0.0 | 56.0 |

These results are further represented by the graph in FIG. 1. As can be seen in FIG. 1 and in light of the results in Table 3, the pain felt by the patients decreased on average by 71.7%.

At the end of 10 days of applying the composition according to the invention, the "pain" dimension of the WOMAC went from 57.1±7.4 at inclusion to 14.3±13.8 at the end of the study, i.e., a significant reduction of 42.7±17.1 points (p<0.0001). The reductions for the other dimensions were also significant, from 54.3±19.1 to 20.8±21.8 for the WOMAC "stiffness" dimension (difference of 33.5±27.8, p<0.01) and from 41.5±17.9 to 11.0±15.9 for the WOMAC "function" dimension (difference of 30.4±21.7, p<0.001). The total WOMAC score also decreased significantly from 45.8±14.3 to 12.5±15.0, i.e., a decrease of 33.2±20.2 points (p<0.001) and a reduction of 72.7% of the score.

The Lequesne algofunctional score decreased significantly between inclusion and the end of the study, from 8.0±2.4 to 3.8±2.9 (p<0.001), i.e., a 52.5% reduction in the score. At the end of the study, two thirds of the patients (66.7%) had no handicap or only a slight handicap.

At the end of the study, 91.7% of the volunteers felt an improvement in their pain, including 2 considerably (16.7%), 8 very much (66.7%) and 1 slightly (8.3%). 91.7% of the volunteers were satisfied with the progression of their gonalgia, including 41.7% very satisfied.

Organoleptically, all patients found the gel easy to apply (83.3% very easy), easily penetrated the skin (75% very easy), had a pleasant texture (50% very pleasant) and a pleasant smell (66.7% pleasant and 33.3% quite pleasant).

All patients would be inclined to use the gel again if they had the same joint pain (41.7% of them very likely) and to recommend it to a relative who had the same knee pain (41.7% of them very likely).

No volunteers experienced any side effects following the use of the composition according to the invention, nor did they develop any allergies.

NMN, a pharmaceutically acceptable derivative thereof, or a pharmaceutically acceptable salt thereof, as well as compositions comprising same, are therefore effective in reducing joint pain induced by physical activity or sports.

Indeed, regardless of the pain measurement scale used, a significant reduction in pain induced by physical activity was measured in the study participants.

Although these results were obtained by measuring joint pain in the knee, NMN, a pharmaceutically acceptable derivative thereof, or a pharmaceutically acceptable salt thereof, as well as compositions comprising same, can be used to treat or prevent other types of joint pain such as, for example, shoulder, elbow, ankle, neck, or other joint pain.

The invention claimed is:

1. A method of treatment of joint pain induced by physical activity, comprising topically administrating nicotinamide mononucleotide (NMN), a pharmaceutically acceptable derivative thereof, or a pharmaceutically acceptable salt thereof.

2. The method according to claim 1, wherein the pharmaceutically acceptable derivative of NMN is selected from dihydronicotinamide mononucleotide (NMN-H), alpha-NMN, a compound of formula (I):

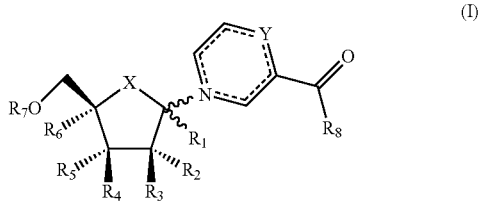

(I)

or a stereoisomer, salt, hydrate, solvate, or pharmaceutically acceptable crystal thereof, wherein:

X is selected from O, $CH_2$, S, Se, CHF, $CF_2$, and $C=CH_2$;

$R_1$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$ alkyl;

$R_2$, $R_3$, $R_4$, and $R_5$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR; wherein R is selected from H, $C_1$-$C_{12}$ alkyl, C(O)($C_1$-$C_{12}$)alkyl, C(O)NH($C_1$-$C_{12}$)alkyl, C(O)O($C_1$-$C_{12}$)alkyl, C(O)aryl, C(O)($C_1$-$C_{12}$)aryl alkyl, C(O)NH($C_1$-$C_{12}$)aryl alkyl, C(O)O($C_1$-$C_{12}$) aryl alkyl, and C(O)CHR$_{AA}$NH$_2$; wherein R$_{AA}$ is a side chain selected from a proteinogenic amino acid;

$R_6$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$ alkyl;

$R_7$ is selected from H, P(O)$R_9R_{10}$, and P(S)$R_9R_{10}$, and

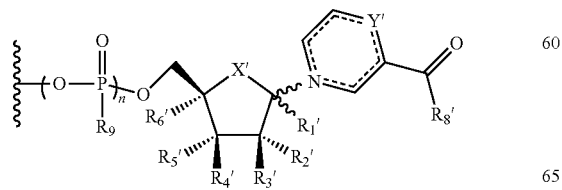

where n is an integer selected from 1, 2, or 3; wherein $R_9$ and $R_{10}$ are independently selected from OH, $OR_{11}$, $NHR_{13}$, $NR_{13}R_{14}$, $C_1$-$C_8$ alkyl, $C_2$-$C_8$ alkenyl, $C_2$-$C_8$ alkynyl, $C_3$-$C_{10}$ cycloalkyl, $C_5$-$C_{12}$ aryl ($C_1$-$C_8$)aryl alkyl, ($C_1$-$C_8$)aryl alkyl, ($C_1$-$C_8$) heteroalkyl, ($C_1$-$C_8$) heterocycloalkyl, heteroaryl, and NHCHR$_A$R$_A$C(O)R$_{12}$; wherein:

$R_{11}$ is selected from $C_1$-$C_{10}$ alkyl, $C_3$-$C_{10}$ cycloalkyl, $C_5$-$C_{18}$ aryl, $C_1$-$C_{10}$ alkyl aryl, $C_5$-$C_{12}$ substituted aryl, $C_1$-$C_{10}$ heteroalkyl, $C_3$-$C_{10}$ heterocycloalkyl, $C_1$-$C_{10}$ haloalkyl, heteroaryl, —(CH$_2$)$_n$C(O)($C_1$-$C_{15}$)alkyl, —(CH$_2$)$_n$OC(O)($C_1$-$C_{15}$)alkyl, —(CH$_2$)$_n$OC(O)O($C_1$-$C_{15}$)alkyl, —(CH$_2$)$_n$SC(O) ($C_1$-$C_{15}$)alkyl, —(CH$_2$)$_n$C(O)O($C_1$-$C_{15}$)alkyl, and —(CH$_2$)$_n$C(O)O($C_1$-$C_{15}$)alkyl aryl; wherein n is an integer selected from 1 to 8; P(O)(OH)OP(O)(OH)$_2$, halogen, nitro, cyano, $C_1$-$C_6$ alkoxy, $C_1$-$C_6$ haloalkoxy, —N(R$_{11a}$)$_2$, $C_1$-$C_6$ acylamino, —COR$_{11b}$, —O COR$_{11b}$; NHSO$_2$($C_1$-$C_6$ alkyl), —SO$_2$N(R$_{11a}$)$_2$ SO$_2$ wherein each R$_{11a}$ is independently selected from H and $C_1$-$C_6$ alkyl and R$_{11b}$ is independently selected from OH, $C_1$-$C_6$ alkoxy, NH($C_1$-$C_6$ alkyl) or N($C_1$-$C_6$ alkyl)$_2$;

$R_{12}$ is selected from H, $C_1$-$C_{10}$ alkyl, $C_2$-$C_8$ alkenyl, $C_2$-$C_8$ alkynyl, $C_1$-$C_{10}$ haloalkyl, $C_3$-$C_{10}$ cycloalkyl, $C_3$-$C_{10}$ heterocycloalkyl, $C_5$-$C_{18}$ aryl, $C_1$-$C_4$ alkyl aryl, and $C_5$-$C_{12}$ heteroaryl; wherein said aryl or heteroaryl groups are optionally substituted with one or two groups selected from halogen, trifluoromethyl, $C_1$-$C_6$ alkyl, $C_1$-$C_6$ alkoxy, and cyano; and $R_A$ and $R_{A'}$ are independently selected from H, $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ thioalkyl, $C_1$-$C_{10}$ hydroxylalkyl, $C_1$-$C_{10}$ alkyl aryl, and $C_5$-$C_{12}$ aryl, $C_3$-$C_{10}$ heterocycloalkyl, heteroaryl, —(CH$_2$)$_3$NHC(=NH)NH$_2$, (1H-indol-3-yl)methyl, (1H-imidazol-4-yl)methyl, and a side chain selected from a proteinogenic amino acid or a non-proteinogenic amino acid; wherein said aryl groups are optionally substituted with a group selected from hydroxyl, $C_1$-$C_{10}$ alkyl, $C_1$-$C_6$ alkoxy, halogen, nitro, and cyano; or $R_9$ and $R_{10}$ together with the phosphorus atoms to which they are attached form a 6-membered ring wherein —$R_9$-$R_{10}$— represents CH$_2$—CH$_2$— CHR—; wherein R is selected from H, ($C_5$-$C_6$) aryl, and ($C_5$-$C_6$) heteroaryl, wherein said aryl or heteroaryl groups are optionally substituted with halogen, trifluoromethyl, $C_1$-$C_6$ alkyl, $C_1$-$C_6$ alkoxy, and cyano; or $R_9$ and $R_{10}$ together with the phosphorus atoms to which they are attached form a 6-membered ring, wherein —$R_9$-$R_{10}$— represents-O—CH$_2$—CH$_2$— CHR—O—; wherein R is selected from H, ($C_5$-$C_6$) aryl, and ($C_5$-$C_6$) heteroaryl, wherein said aryl or heteroaryl groups are optionally substituted with halogen, trifluoromethyl, ($C_1$-$C_6$) alkyl, ($C_1$-$C_6$) alkoxy, and cyano;

$R_8$ is selected from H, OR, NHR$_{13}$, NR$_{13}$R$_{14}$, NH—NHR$_{13}$, SH, CN, N$_3$, and halogen;

wherein R$_{13}$ and R$_{14}$ are independently selected from H, ($C_1$-$C_8$) alkyl, and ($C_1$-$C_8$) alkyl aryl, and-CR$_B$R$_C$—C(O)—ORD, wherein R$_B$ and R$_C$ are independently hydrogen, ($C_1$-$C_6$) alkyl, ($C_1$-$C_6$) alkoxy benzyl, indolyl, or imidazolyl, wherein the ($C_1$-$C_6$) alkyl and the ($C_1$-$C_6$) alkoxy can be optionally and independently of each other substituted by one or more of halogen, amino, amido, guanidyl, hydroxyl, thiol, or carboxyl, and the benzyl group is optionally substituted by one or more of the halogen or hydroxyl groups, or $R_B$ and $R_C$ together with the carbon atom to which they are attached form a $C_3$-$C_6$ cycloalkyl group optionally substituted by one or more of halogen, amino, amido, guanidyl, hydroxyl, thiol, and carboxyl, and $R_D$ is hydrogen, $(C_1$-$C_6)$ alkyl, $(C_2$-$C_6)$ alkenyl, $(C_2$-$C_6)$ alkynyl, or $(C_3$-$C_6)$ cycloalkyl;

Y is selected from CH, $CH_2$, $C(CH_3)_2$, and $CCH_3$;

⎓ represents a single or double bond depending on Y; and

∿ represents the alpha or beta anomer depending on the position of $R_1$ or a compound of formula (Ia):

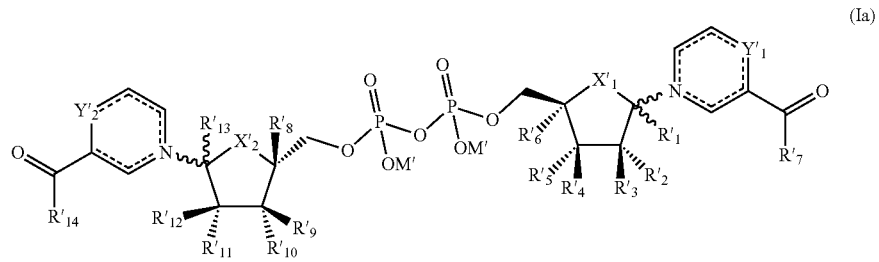

(Ia)

or a stereoisomer, salt, hydrate, solvate, or crystal thereof, wherein $X'_1$ and $X'_2$ are independently selected from O, $CH_2$, S, Se, CHF, $CF_2$, and $C=CH_2$;

$R'_1$ and $R'_{13}$ are independently selected from H, azido, cyano, $C_1$-$C_8$ alkyl, $C_1$-$C_8$ thioalkyl, $C_1$-$C_8$ heteroalkyl, and OR, wherein R is selected from H and $C_1$-$C_8$ alkyl, $R'_2$, $R'_3$, $R'_4$, $R'_5$, $R'_9$, $R'_{10}$, $R'_{11}$, and $R'_{12}$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR, wherein R may be selected from H, $C_1$-$C_{12}$ alkyl, $C(O)(C_1$-$C_{12})$ alkyl, $C(O)NH(C_1$-$C_{12})$ alkyl, $C(O)O(C_1$-$C_{12})$ alkyl, C(O) aryl, $C(O)(C_1$-$C_{12})$ aryl, $C(O)NH(C_1$-$C_{12})$ aryl alkyl, $C(O)O(C_1$-$C_{12})$ aryl alkyl, or a C(O)CHR$_{AA}$NH2 group, wherein R$_{AA}$ is a side chain selected from a proteogenic amino acid;

$R'_6$ and $R'_8$ are independently selected from H, azido, cyano, $C_1$-$C_8$ alkyl, and OR, wherein R is selected from H, and $C_1$-$C_8$ alkyl;

$R'_7$ and $R'_{14}$ are independently selected from H, OR, NHR, NRR', NH—NHR, SH, CN, $N_3$, and halogen, wherein R and R' are independently selected from H and $(C_1$-$C_8)$ aryl alkyl;

$Y'_1$ and $Y'_2$ are independently selected from CH, $CH_2$, $C(CH_3)_2$, or $CCH_3$;

M' is selected from H or a suitable counterion;

⎓ represents a single or double bond depending on $Y'_1$ and $Y'_2$; and

∿ represents an alpha or beta anomer depending on the position of $R'_1$ and $R'_{13}$;

and combinations thereof.

3. The method according to claim 2, wherein the pharmaceutically acceptable derivative of NMN is selected from

| Compounds (anomers) | Structure |
|---|---|
| I-B (alpha) | ![structure] |
| I-C (beta) | ![structure] |
| I-D (alpha) | ![structure] |
| I-E (beta) | ![structure] |
| I-F (alpha) | ![structure] |

| Compounds (anomers) | Structure |
|---|---|
| I-G (beta) | 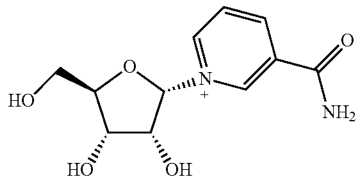 |
| I-H (alpha) | 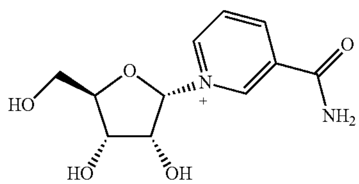 |
| I-I (beta) | 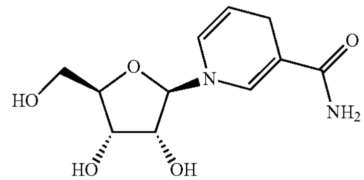 [SMILES: NC(=O)C1=CN([C@@H]2O[C@H](CO)[C@@H](O)[C@H]2O)C=CC1] |
| I-J (alpha) | | and combinations thereof.

4. The method according to claim 2, wherein the pharmaceutically acceptable derivative of NMN is selected from

| Compounds (anomers) | Structure |
|---|---|
| Ia-A (beta, beta) | 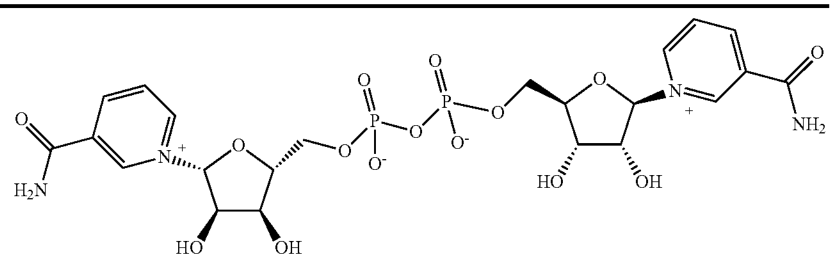 |
| Ia-B (beta, alpha) | 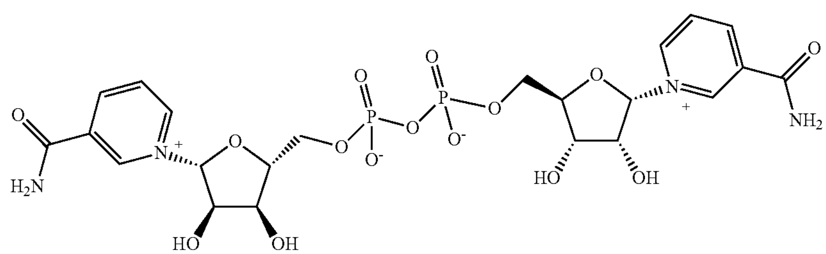 |
| Ia-C (alpha, alpha) | 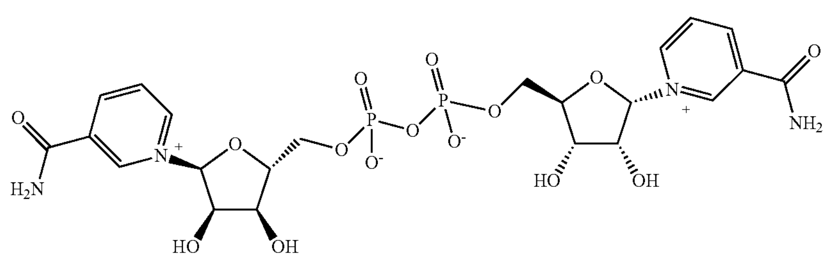 |
| Ia-D (beta, beta) | 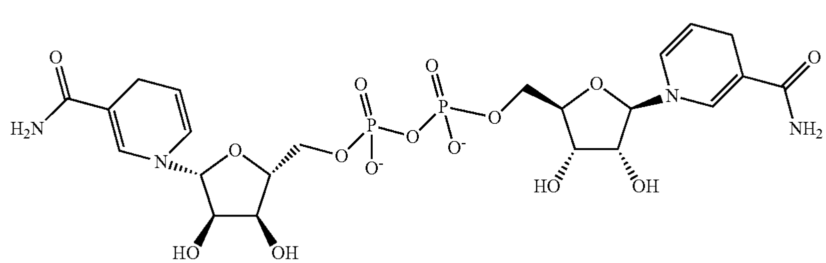 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |

| Compounds (anomers) | Structure |
|---|---|
| Ia-E (beta, alpha) | 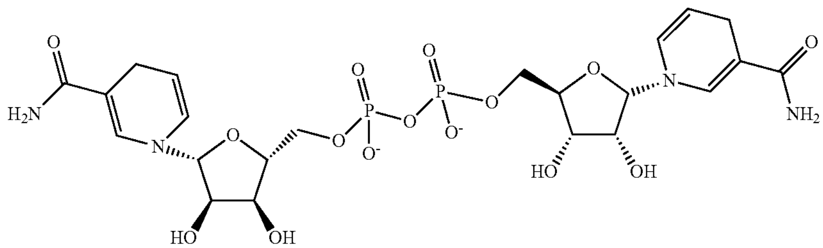 |
| Ia-F (alpha, alpha) | 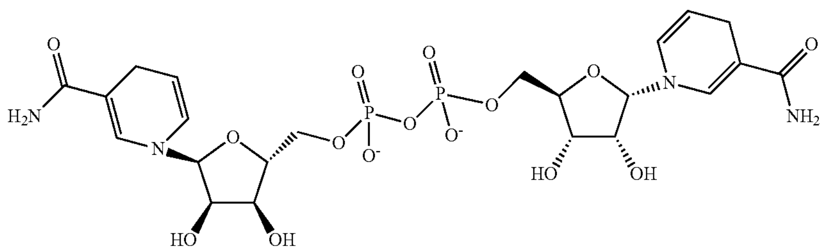 [SMILES: NC(=O)C1=CN([C@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| Ia-G (beta, beta) | 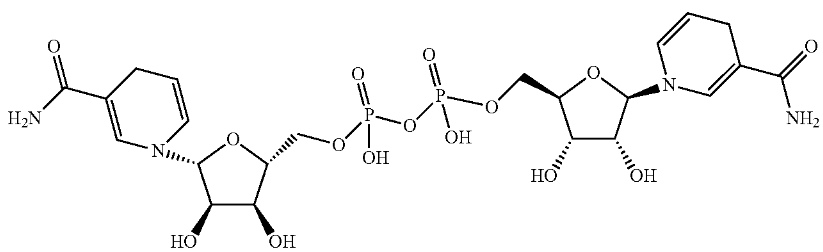 [SMILES: NC(=O)C1=CN([C@@H]2O[C@H](COP(=O)(O)OP(=O)(O)OC[C@H]3O[C@@H](N4C=CCC(C(N)=O)=C4)[C@H](O)[C@@H]3O)[C@@H](O)[C@H]2O)C=CC1] |
| Ia-H (beta, alpha) | 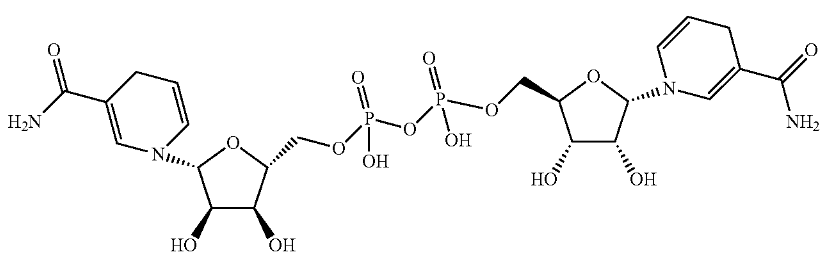 [SMILES: NC(=O)C1=CN([C@@H]2O[C@H](COP(=O)(O)OP(=O)(O)OC[C@H]3O[C@H](N4C=CCC(C(N)=O)=C4)[C@H](O)[C@@H]3O)[C@@H](O)[C@H]2O)C=CC1] |
| Ia-I (alpha, alpha) | 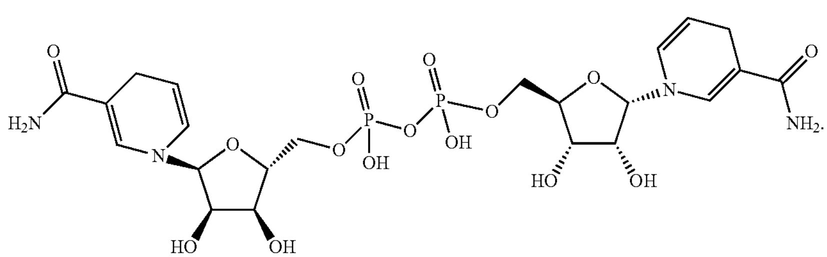 [SMILES: NC(=O)C1=CN([C@H]2O[C@H](COP(=O)(O)OP(=O)(O)OC[C@H]3O[C@H](N4C=CCC(C(N)=O)=C4)[C@H](O)[C@@H]3O)[C@@H](O)[C@H]2O)C=CC1] |

5. The method according to claim 2, wherein the joint pain involves the neck, shoulder, scapula, elbow, wrist, hand joints, hip, sacroiliac joint, knee, ankle, foot joints, or combinations thereof, preferably the knee.

6. The method according to claim 2, wherein the physical activity is playing sports.

7. The method according to claim 2, wherein the nicotinamide mononucleotide (NMN), the pharmaceutically acceptable derivative thereof, or the pharmaceutically acceptable salt thereof can be used in combination with at least one other therapeutic agent.

8. The method according to claim 2, wherein the joint pain is not due to any of the pathologies selected from a tumor, arthritis, gout, osteoarthritis, joint deformity, connective tissue disease, dorsopathy, neurodegenerative disease neuropathy, genetic disease, autoimmune disease, myopathy, osteopathy, osteoporosis, chondropathy, vasculopathy, viral infection, fungal infection, bacterial infection, parasite, side effect of a drug, surgical procedure, medical examination, calcification, trauma unless induced by physical activity, malformation, and combinations thereof.

9. A method of treatment of joint pain induced by physical activity, the method comprising the step of topically administering a composition comprising nicotinamide mononucleotide (NMN), a pharmaceutically acceptable derivative thereof, or a pharmaceutically acceptable salt thereof, and at least one pharmaceutically acceptable excipient.

10. The method according to claim 9, wherein the composition comprises nicotinamide mononucleotide (NMN), the pharmaceutically acceptable derivative thereof, or the pharmaceutically acceptable salt thereof, in an amount between 0.05% and 15% by weight.

11. The method according to claim 9, wherein the composition is in the form of a water-in-oil emulsion or an oil-in-water emulsion.

12. The method according to claim 9, wherein the composition further comprises at least one additional therapeutic agent.

13. The method according to claim 12, wherein the at least one additional therapeutic agent is selected from an analgesic, a non-steroidal anti-inflammatory, cortisone, a cortisone derivative, or combinations thereof.

14. The method according to claim 9, wherein the pharmaceutically acceptable derivative is selected from dihydronicotinamide mononucleotide (NMN-H), alpha-NMN, a compound of formula (I):

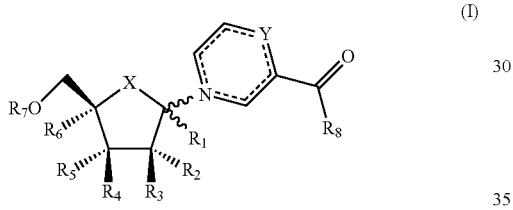

or a stereoisomer, salt, hydrate, solvate, or pharmaceutically acceptable crystal thereof, wherein:

X is selected from O, $CH_2$, S, Se, CHF, $CF_2$, and $C=CH_2$;

$R_1$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$ alkyl;

$R_2$, $R_3$, $R_4$ and $R_5$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR; wherein R is selected from H, $C_1$-$C_{12}$ alkyl, C(O)($C_1$-$C_{12}$)alkyl, C(O)NH($C_1$-$C_{12}$)alkyl, C(O)O($C_1$-$C_{12}$)alkyl, C(O)aryl, C(O)($C_1$-$C_{12}$)aryl alkyl, C(O)NH($C_1$-$C_{12}$)aryl alkyl, C(O)O($C_1$-$C_{12}$) aryl alkyl, and C(O)CHR$_{AA}$ NH$_2$; wherein R$_{AA}$ is a side chain selected from a proteinogenic amino acid;

$R_6$ is selected from H, azido, cyano, $C_1$-$C_8$ alkyl, $C_1$-$C_8$ thioalkyl, $C_1$-$C_8$ heteroalkyl, and OR; wherein R is selected from H and $C_1$-$C_8$ alkyl;

$R_7$ is selected from H, P(O)$R_9R_{10}$ and P(S)$R_9R_{10}$ and

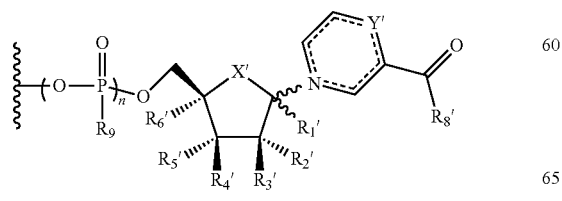

where n is an integer selected from 1, 2, or 3; wherein $R_9$ and $R_{10}$ are independently selected from OH, OR$_{11}$, NHR$_{13}$, NR$_{13}$ R$_{14}$, $C_1$-$C_8$ alkyl, $C_2$-$C_8$ alkenyl, $C_2$-$C_8$ alkynyl, $C_3$-$C_{10}$ cycloalkyl, $C_5$-$C_{12}$ aryl ($C_1$-$C_8$)aryl alkyl, ($C_1$-$C_8$)aryl alkyl, ($C_1$-$C_8$) heteroalkyl, ($C_1$-$C_8$) heterocycloalkyl, heteroaryl, and NHCHR$_A$R$_A$,C(O)R$_{12}$; wherein $R_{11}$ is selected from $C_1$-$C_{10}$ alkyl, $C_3$-$C_{10}$ cycloalkyl, $C_5$-$C_{18}$ aryl, $C_1$-$C_{10}$ alkyl aryl, $C_5$-$C_{12}$ substituted aryl, $C_1$-$C_{10}$ heteroalkyl, $C_3$-$C_{10}$ heterocycloalkyl, $C_1$-$C_{10}$ haloalkyl, heteroaryl, —($CH_2$)$_n$C(O)($C_1$-$C_{15}$)alkyl, —($CH_2$)$_n$OC(O)($C_1$-$C_{15}$)alkyl, —($CH_2$)$_n$OC(O)O($C_1$-$C_{15}$)alkyl, —($CH_2$)$_n$SC(O) ($C_1$-$C_{15}$)alkyl, —($CH_2$)$_n$ C(O)O($C_1$-$C_{15}$)alkyl, and —($CH_2$)$_n$ C(O)O($_1$-$C_{15}$)alkyl aryl; wherein n is an integer selected from 1 to 8; P(O)(OH)OP(O)(OH)$_2$, halogen, nitro, cyano, $C_1$-$C_6$ alkoxy, $C_1$-$C_6$ haloalkoxy, —N($R_{11a}$)$_2$, $C_1$-$C_6$ acylamino, —COR$_{11b}$, —O COR$_{11b}$; NHSO$_2$ ($C_1$-$C_6$ alkyl), —SO$_2$N($R_{11a}$)$_2$ SO$_2$, wherein each $R_{11a}$ is independently selected from H and a $C_1$-$C_6$ alkyl, and $R_{11b}$ is independently selected from OH, $C_1$-$C_6$ alkoxy, NH($C_1$-$C_6$ alkyl), or N($C_1$-$C_6$ alkyl)$_2$;

$R_{12}$ is selected from H, $C_1$-$C_{10}$ alkyl, $C_2$-$C_8$ alkenyl, $C_2$-$C_8$ alkynyl, $C_1$-$C_{10}$ haloalkyl, $C_3$-$C_{10}$ cycloalkyl, $C_3$-$C_{10}$ heterocycloalkyl, $C_5$-$C_{18}$ aryl, $C_1$-$C_4$ alkyl aryl, and $C_5$-$C_{12}$ heteroaryl; wherein said aryl or heteroaryl groups are optionally substituted with one or two groups selected from halogen, trifluoromethyl, $C_1$-$C_6$ alkyl, $C_1$-$C_6$ alkoxy, and cyano; and $R_A$ and $R_{A'}$ are independently selected from H, $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ thioalkyl, $C_1$-$C_{10}$ hydroxylalkyl, $C_1$-$C_{10}$ alkyl aryl, and $C_5$-$C_{12}$ aryl, $C_3$-$C_{10}$ heterocycloalkyl heteroaryl, —($CH_2$)$_3$NHC(=NH)NH$_2$, (1H-indol-3-yl)methyl, (1H-imidazol-4-yl)methyl, and a side chain selected from a proteinogenic amino acid or a non-proteinogenic amino acid; wherein said aryl groups are optionally substituted with a group selected from hydroxyl, $C_1$-$C_{10}$ alkyl, $C_1$-$C_6$ alkoxy, halogen, nitro, and cyano; or $R_9$ and $R_{10}$ together with the phosphorus atoms to which they are attached form a 6-membered ring wherein —$R_9$—$R_{10}$— represents $CH_2$—$CH_2$—CHR—; wherein R is selected from H, ($C_5$-$C_6$) aryl and ($C_5$-$C_6$) heteroaryl, wherein said aryl or heteroaryl groups are optionally substituted with halogen, trifluoromethyl, $C_1$-$C_6$ alkyl, $C_1$-$C_6$ alkoxy, and cyano; or $R_9$ and $R_{10}$ together with the phosphorus atoms to which they are attached form a 6-membered ring, wherein —$R_9$—$R_{10}$— represents —O—$CH_2$—$CH_2$—CHR—O—; wherein R is selected from H, ($C_5$-$C_6$) aryl, and ($C_5$-$C_6$) heteroaryl, wherein said aryl or heteroaryl groups are optionally substituted with halogen, trifluoromethyl, ($C_1$-$C_6$) alkyl, ($C_1$-$C_6$) alkoxy, and cyano;

$R_8$ is selected from H, OR, NHR$_{13}$, NR$_{13}$ R$_{14}$, NH—NHR$_{13}$, SH, CN, N$_3$, and halogen;

wherein $R_{13}$ and $R_{14}$ are independently selected from H, ($C_1$-$C_8$) alkyl, and ($C_1$-$C_8$) alkyl aryl, and —CR$_B$ R$_C$—C(O)—OR$_D$, wherein R$_B$ and R$_C$ are independently hydrogen, ($C_1$-$C_6$) alkyl, ($C_1$-$C_6$) alkoxy benzyl, indolyl, or imidazolyl, wherein the ($C_1$-$C_6$) alkyl and the ($C_1$-$C_6$) alkoxy can be optionally and independently of each other substituted by one or more of halogen, amino, amido, guanidyl, hydroxyl, thiol, or carboxyl, and the benzyl group is optionally substituted by one or more of the halogen or hydroxyl groups, or $R_B$ and $R_C$ together with the carbon atom to which they are attached form a $C_3$-$C_6$ cycloalkyl group optionally substituted by one or more of halogen, amino, amido, guanidyl, hydroxyl, thiol, and carboxyl, and $R_D$ is hydrogen, ($C_1$-$C_6$) alkyl, ($C_2$-$C_6$) alkenyl, ($C_2$-$C_6$) alkynyl, or ($C_3$-$C_6$) cycloalkyl;

Y is selected from CH, $CH_2$, $C(CH_3)_2$, and $CCH_3$;

⌇⌇⌇ represents a single or double bond depending on Y; and

∿∿∿ represents the alpha or beta anomer depending on the position of $R_1$ or a compound of formula (Ia):

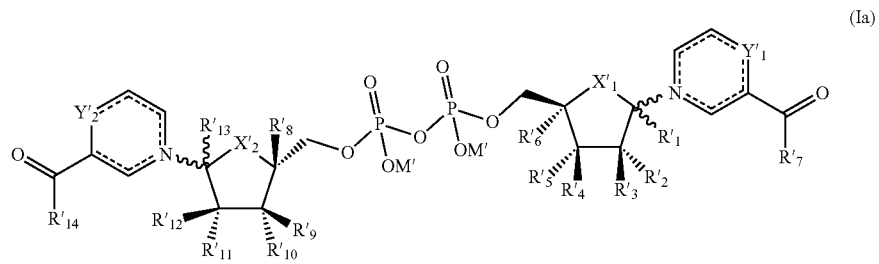

(Ia)

or a stereoisomer, salt, hydrate, solvate, or crystal thereof, wherein $X'_1$ and $X'_2$ are independently selected from O, $CH_2$, S, Se, CHF, $CF_2$, and C=$CH_2$;

$R'_1$ and $R'_{13}$ are independently selected from H, azido, cyano, $C_1$-$C_8$ alkyl, $C_1$-$C_8$ thioalkyl, $C_1$-$C_8$ heteroalkyl, and OR, wherein R is selected from H and $C_1$-$C_8$ alkyl, $R'_2$, $R'_3$, $R'_4$, $R'_5$, $R'_9$, $R'_{10}$, $R'_{11}$, and $R'_{12}$ are independently selected from H, halogen, azido, cyano, hydroxyl, $C_1$-$C_{12}$ alkyl, $C_1$-$C_{12}$ thioalkyl, $C_1$-$C_{12}$ heteroalkyl, $C_1$-$C_{12}$ haloalkyl, and OR, wherein R may be selected from H, $C_1$-$C_{12}$ alkyl, C(O)($C_1$-$C_{12}$) alkyl, C(O)NH($C_1$-$C_{12}$) alkyl, C(O)O($C_1$-$C_{12}$) alkyl, C(O) aryl, C(O)($C_1$-$C_{12}$) aryl, C(O)NH($C_1$-$C_{12}$) aryl alkyl, C(O)O($C_1$-$C_{12}$) aryl alkyl, or a C(O) CHR$_{AA}$NH2 group, wherein R$_{AA}$ is a side chain selected from a proteogenic amino acid;

$R'_6$ and $R'_8$ are independently selected from H, azido, cyano, $C_1$-$C_8$ alkyl, and OR, wherein R is selected from H and $C_1$-$C_8$ alkyl;

$R'_7$ and $R'_{14}$ are independently selected from H, OR, NHR, NRR', NH—NHR, SH, CN, $N_3$, and halogen, wherein R and R' are independently selected from H and ($C_1$-$C_8$) aryl alkyl;

$Y'_1$ and $Y'_2$ are independently selected from CH, $CH_2$, $C(CH_3)_2$, or $CCH_3$;

M' is selected from H or a suitable counterion;

⌇⌇⌇ represents a single or double bond depending on $Y'_1$ and $Y'_2$; and

∿∿∿ represents an alpha or beta anomer depending on the position of $R'_1$ and $R'_{13}$;

and combinations thereof.

15. The method of claim 14, wherein the pharmaceutically acceptable derivative of NMN is selected from

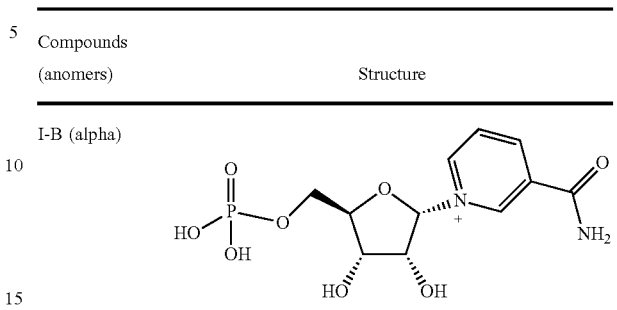

| Compounds (anomers) | Structure |
|---|---|
| I-B (alpha) | 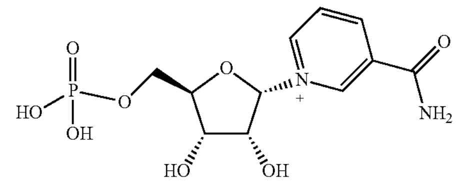 |

-continued

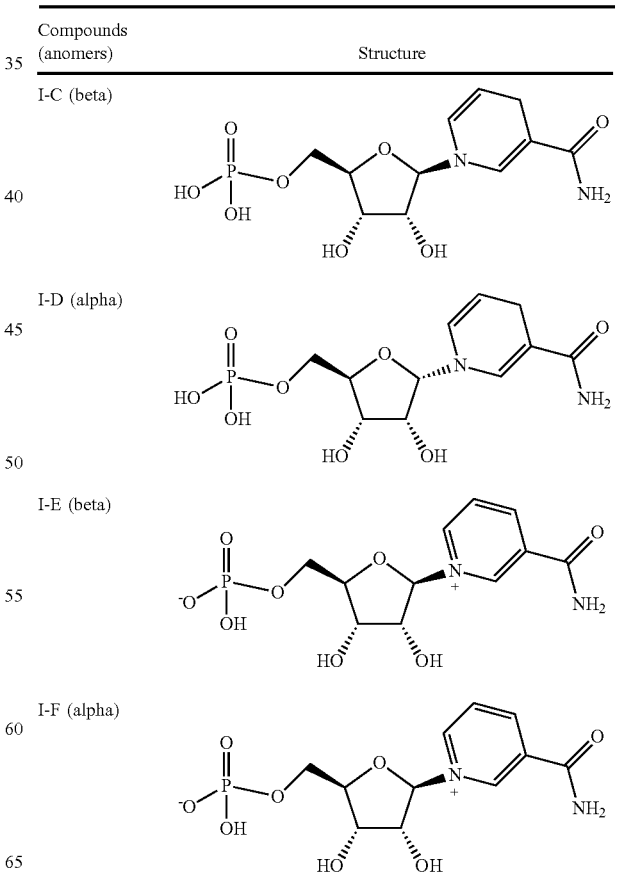

| Compounds (anomers) | Structure |
|---|---|
| I-C (beta) | 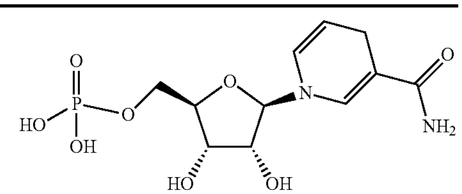 |
| I-D (alpha) | 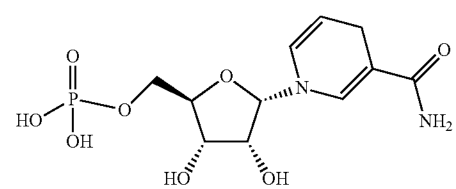 [SMILES: NC(=O)C1=CN([C@H]2O[C@H](COP(=O)(O)O)[C@@H](O)[C@H]2O)C=CC1] |
| I-E (beta) | 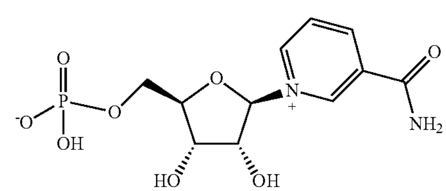 |
| I-F (alpha) | 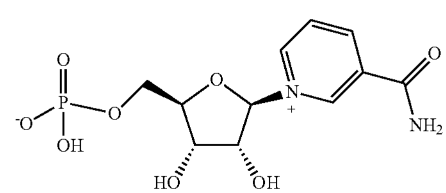 |

-continued
| Compounds (anomers) | Structure |
|---|---|
| I-G (beta) | 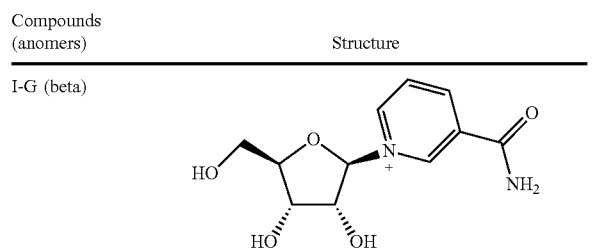 |
| I-H (alpha) | 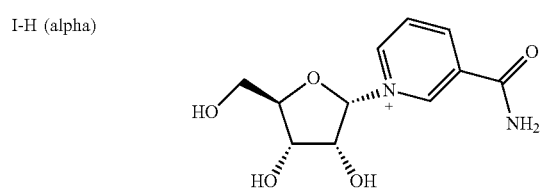 |
-continued
| Compounds (anomers) | Structure |
|---|---|
| I-I (beta) | 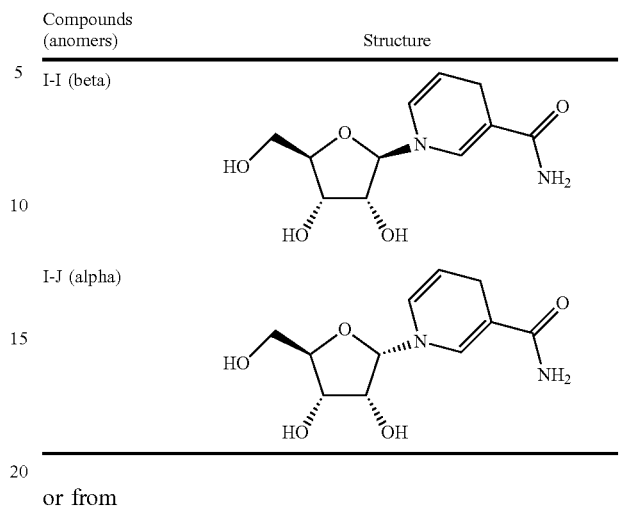 |
| I-J (alpha) | 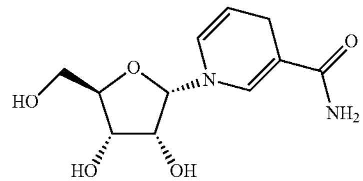 [SMILES: NC(=O)C1=CN([C@H]2O[C@H](CO)[C@@H](O)[C@H]2O)C=CC1] |
or from
| Compounds (anomers) | Structure |
|---|---|
| Ia-A (beta, beta) | 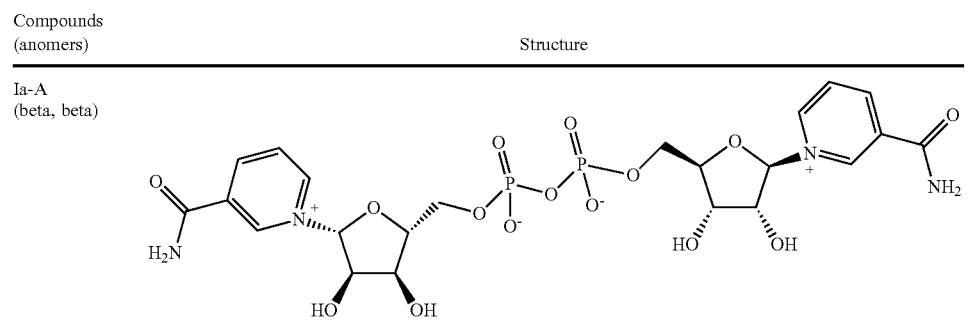 |
| Ia-B (beta, alpha) | 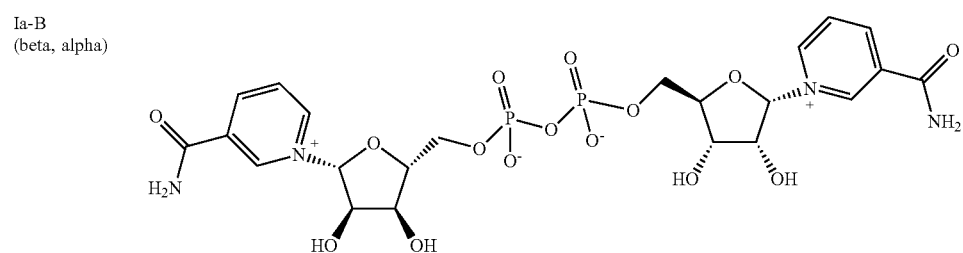 |
| Ia-C (alpha, alpha) | 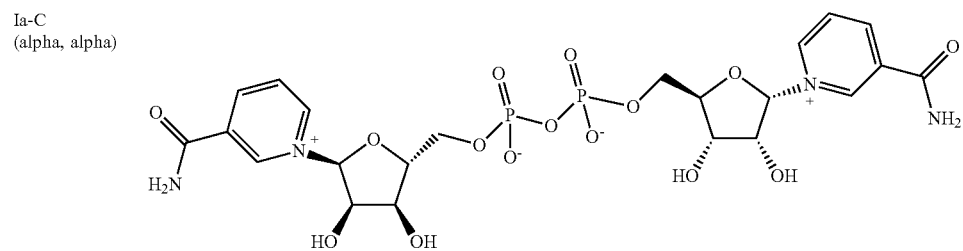 |
| Ia-D (beta, beta) | 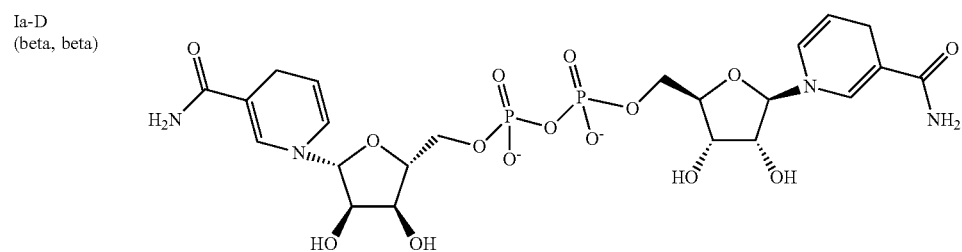 |

-continued

| Compounds (anomers) | Structure |
|---|---|
| Ia-E (beta, alpha) | 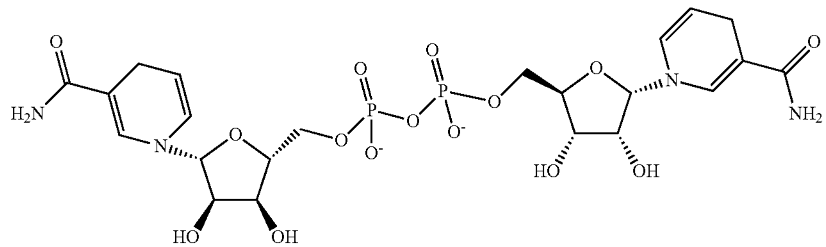 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| Ia-F (alpha, alpha) | 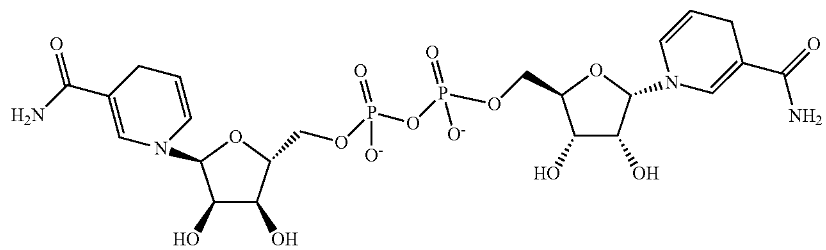 [SMILES: NC(=O)C1=CN([C@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| Ia-G (beta, beta) | 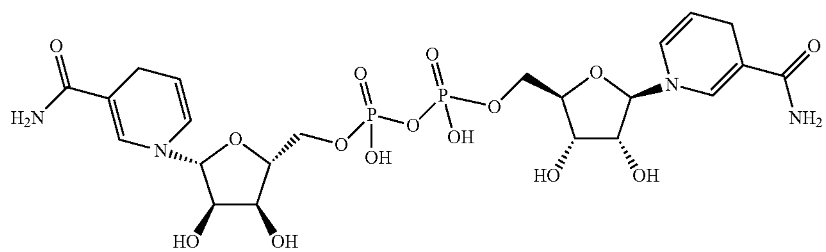 [SMILES: NC(=O)C1=CN([C@@H]2O[C@H](COP(=O)(O)OP(=O)(O)OC[C@H]3O[C@@H](N4C=CCC(C(N)=O)=C4)[C@H](O)[C@@H]3O)[C@@H](O)[C@H]2O)C=CC1] |
| Ia-H (beta, alpha) | 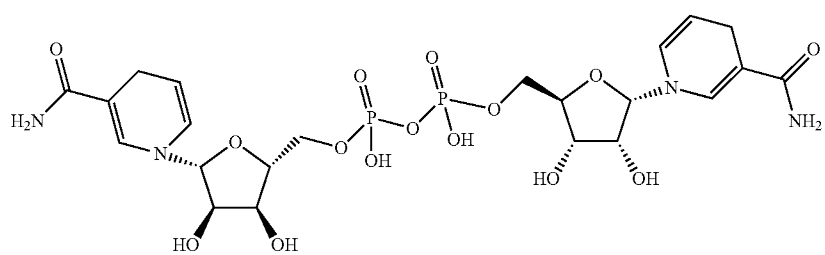 [SMILES: NC(=O)C1=CN([C@@H]2O[C@H](COP(=O)(O)OP(=O)(O)OC[C@H]3O[C@H](N4C=CCC(C(N)=O)=C4)[C@H](O)[C@@H]3O)[C@@H](O)[C@H]2O)C=CC1] |
| Ia-I (alpha, alpha) | | and combination thereof.

* * * * *